US008968686B2

(12) United States Patent
Shaikh et al.

(10) Patent No.: US 8,968,686 B2
(45) Date of Patent: *Mar. 3, 2015

(54) OXIDATION SYSTEM WITH SIDEDRAW SECONDARY REACTOR

(75) Inventors: Ashfaq Shaikh, Kingsport, TN (US); Alan George Wonders, Longview, TX (US)

(73) Assignee: Grupo Petrotemex, S.A. de C.V., San Pedro Garza Garcia (MX)

( * ) Notice: Subject to any disclaimer, the term of this patent is extended or adjusted under 35 U.S.C. 154(b) by 801 days.

This patent is subject to a terminal disclaimer.

(21) Appl. No.: 12/957,733

(22) Filed: Dec. 1, 2010

(65) Prior Publication Data

US 2011/0190537 A1    Aug. 4, 2011

Related U.S. Application Data

(60) Provisional application No. 61/299,450, filed on Jan. 29, 2010, provisional application No. 61/299,453, filed on Jan. 29, 2010, provisional application No. 61/299,455, filed on Jan. 29, 2010.

(51) Int. Cl.
*B01J 8/18* (2006.01)
*B01J 8/22* (2006.01)
(Continued)

(52) U.S. Cl.
CPC .............. *B01J 8/1872* (2013.01); *B01J 8/1827* (2013.01); *B01J 8/22* (2013.01); *B01J 10/002* (2013.01);
(Continued)

(58) Field of Classification Search
CPC .............. B01J 8/00; B01J 8/18; B01J 8/1809;
B01J 8/1818; B01J 8/1827; B01J 8/1845;
B01J 8/1854; B01J 8/1863; B01J 8/24;
B01J 8/26; B01J 19/00; B01J 19/24; B01J
35/00; B01J 2204/00; B01J 2208/00; B01J
35/02; C07C 1/00; C07C 51/00; C07C 51/16;
C07C 51/21; C07C 51/255; C07C 51/265
USPC ................. 422/129, 139, 187, 600, 630, 642;
562/400, 404, 407–409, 412, 413
See application file for complete search history.

(56) References Cited

U.S. PATENT DOCUMENTS 4,370,496 A * 1/1983 Shigeyasu et al. ............ 562/487
7,355,068 B2 * 4/2008 Wonders et al. .............. 562/413
(Continued)

FOREIGN PATENT DOCUMENTS

CN    101394923 A    3/2009
JP    10-330292    12/1998
(Continued)

OTHER PUBLICATIONS

Office Action issued Sep. 5, 2012 in European Patent Application No. 10795159.2.
(Continued)

*Primary Examiner* — Natasha Young
(74) *Attorney, Agent, or Firm* — Oblon, Spivak, McClelland, Maier & Neustadt, L.L.P.

(57) ABSTRACT

Disclosed are process and apparatus for vertical splitting of the oxygen supply to a post-oxidation reactor. Further disclosed are process and apparatus for supplying reaction medium to a post-oxidation reactor at a mid-level inlet. Such apparatus and process can assist in reducing oxygen pinch throughout the post-oxidation reactor.

22 Claims, 4 Drawing Sheets

(51) Int. Cl.
*B01J 10/00* (2006.01)
*B01J 8/00* (2006.01)
*B01J 19/00* (2006.01)
*B01J 19/24* (2006.01)
*B01J 35/02* (2006.01)
*C07C 51/00* (2006.01)
*C07C 51/16* (2006.01)
*C07C 51/21* (2006.01)
*C07C 51/255* (2006.01)
*C07C 51/265* (2006.01)

(52) U.S. Cl.
CPC ...... *C07C 51/265* (2013.01); *B01J 2208/00911* (2013.01); *B01J 2208/00991* (2013.01); *B01J 2219/00006* (2013.01); *B01J 2219/0004* (2013.01)
USPC ........... 422/642; 422/129; 422/139; 422/187; 422/600; 422/630; 562/407; 562/408; 562/409; 562/412; 562/413

(56) References Cited

U.S. PATENT DOCUMENTS

| | | | |
|---|---|---|---|
| 7,910,769 B2 * | 3/2011 | Wonders et al. | 562/412 |
| 2006/0047143 A1 | 3/2006 | Wonders et al. | |
| 2007/0155985 A1 * | 7/2007 | Wonders et al. | 562/410 |
| 2007/0208194 A1 | 9/2007 | Woodruff et al. | |
| 2007/0292319 A1 | 12/2007 | Woodruff et al. | |
| 2007/0292320 A1 | 12/2007 | Wonders et al. | |
| 2010/0200804 A1 | 8/2010 | Woodruff et al. | |
| 2011/0190536 A1 * | 8/2011 | Shaikh et al. | 562/413 |

FOREIGN PATENT DOCUMENTS

| | | |
|---|---|---|
| JP | 2013-518103 | 5/2013 |
| JP | 2013-518104 | 5/2013 |
| WO | WO 2006/028771 A2 * | 3/2006 |
| WO | WO 2007/081507 A2 | 7/2007 |
| WO | WO 2007/106289 A1 | 9/2007 |

OTHER PUBLICATIONS

International Preliminary Report on Patentability and Written Opinion issued Jul. 31, 2012 in PCT/US2010/059644 filed Dec. 9, 2010.
International Search Report with Written Opinion issued Mar. 17, 2011 in Application No. PCT/US2010/059644.
Combined Chinese Office Action and Search Report issued Jan. 8, 2014 in Patent Application No. 201080065953.6 (with English language translation).
Office Action received on Oct. 23, 2014, in Russian Federation Application No. 2012/136134 filed on Aug. 21, 2012, with English Translation.

* cited by examiner

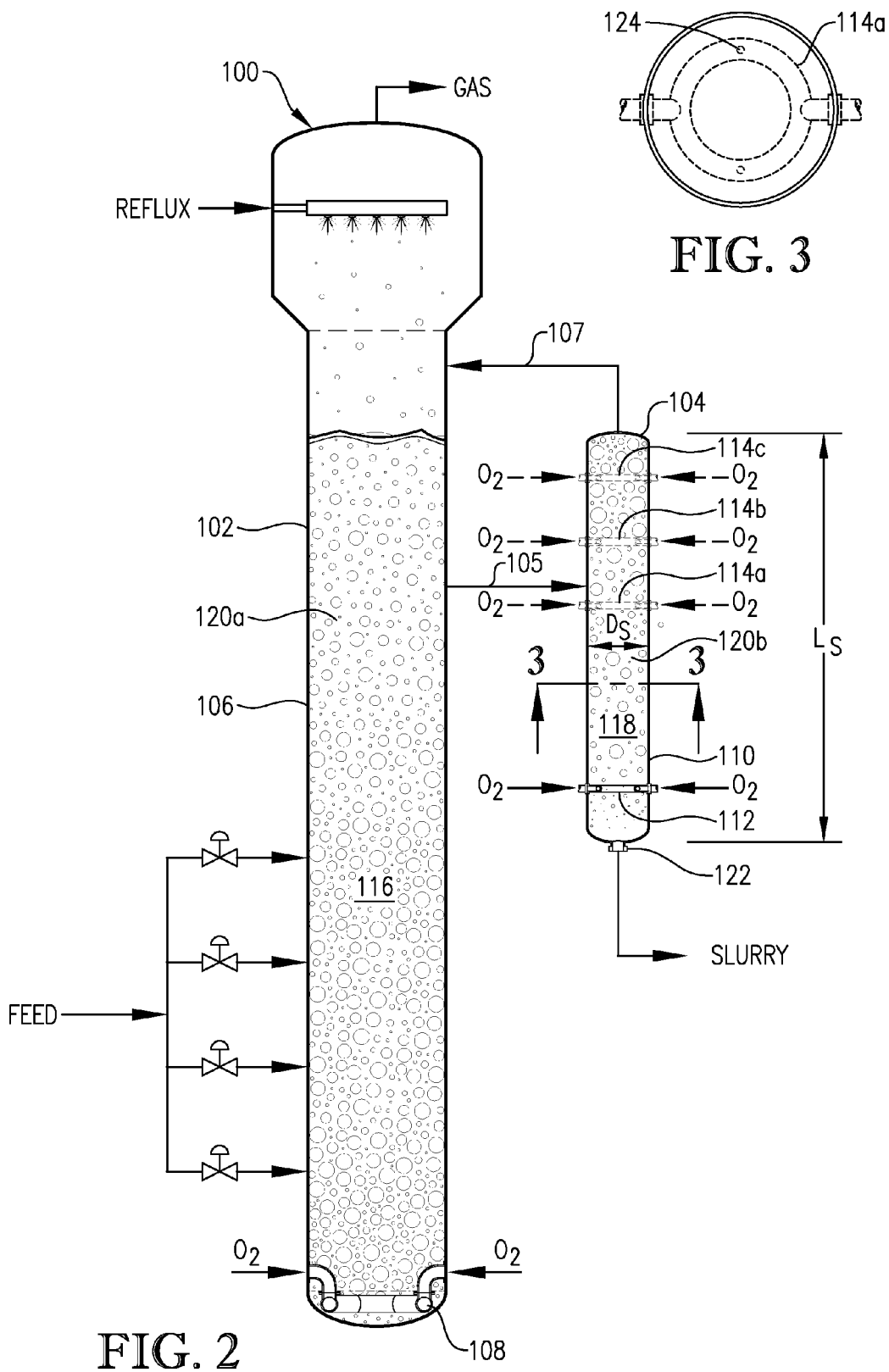

OXIDATION SYSTEM WITH SIDEDRAW SECONDARY REACTOR

CROSS-REFERENCE TO RELATED APPLICATIONS

This application claims priority to the following three U.S. Provisional Application Ser. Nos.: U.S. Provisional Application Ser. No. 61/299,450, filed Jan. 29, 2010, titled "OXIDATION SYSTEM WITH SIDEDRAW SECONDARY REACTOR;" U.S. Provisional Application Ser. No. 61/299,453, filed Jan. 29, 2010, titled "OXIDATION SYSTEM WITH SIDEDRAW SECONDARY REACTOR;" and U.S. Provisional Application Ser. No. 61/299,455, filed Jan. 29, 2010, titled "OXIDATION SYSTEM WITH SIDEDRAW SECONDARY REACTOR," the disclosures of which are incorporated herein by reference in their entirety to the extent they do not contradict statements herein.

BACKGROUND

1. Field of the Invention

This invention relates generally to a process for the production of a polycarboxylic acid composition. One aspect of the invention concerns the partial oxidation of a dialkyl aromatic compound (e.g., para-xylene) to produce a crude aromatic dicarboxylic acid (e.g., crude terephthalic acid), which can thereafter be subjected to purification and separation. Another aspect of the invention concerns an improved reactor system that provides for a more effective and economical oxidation process.

2. Description of the Related Art

Liquid-phase oxidation reactions are employed in a variety of existing commercial processes. For example, liquid-phase oxidation is currently used for the oxidation of aldehydes to acids (e.g., propionaldehyde to propionic acid), the oxidation of cyclohexane to adipic acid, and the oxidation of alkyl aromatics to alcohols, acids, or diacids. A particularly significant commercial oxidation process in the latter category (oxidation of alkyl aromatics) is the liquid-phase catalytic partial oxidation of para-xylene to terephthalic acid. Terephthalic acid is an important compound with a variety of applications. The primary use of terephthalic acid is as a feedstock in the production of polyethylene terephthalate ("PET"). PET is a well-known plastic used in great quantities around the world to make products such as bottles, fibers, and packaging.

In a typical liquid-phase oxidation process, including partial oxidation of para-xylene to terephthalic acid, a liquid-phase feed stream and a gas-phase oxidant stream are introduced into a reactor and form a multi-phase reaction medium in the reactor. The liquid-phase feed stream introduced into the reactor contains at least one oxidizable organic compound (e.g., para-xylene), while the gas-phase oxidant stream contains molecular oxygen. At least a portion of the molecular oxygen introduced into the reactor as a gas dissolves into the liquid phase of the reaction medium to provide oxygen availability for the liquid-phase reaction. If the liquid phase of the multi-phase reaction medium contains an insufficient concentration of molecular oxygen (i.e., if certain portions of the reaction medium are "oxygen-starved"), undesirable side-reactions can generate impurities and/or the intended reactions can be retarded in rate. If the liquid phase of the reaction medium contains too little of the oxidizable compound, the rate of reaction may be undesirably slow. Further, if the liquid phase of the reaction medium contains an excess concentration of the oxidizable compound, additional undesirable side-reactions can generate impurities.

Conventional liquid-phase oxidation reactors are equipped with agitation means for mixing the multi-phase reaction medium contained therein. Agitation of the reaction medium is supplied in an effort to promote dissolution of molecular oxygen into the liquid phase of the reaction medium, maintain relatively uniform concentrations of dissolved oxygen in the liquid phase of the reaction medium, and maintain relatively uniform concentrations of the oxidizable organic compound in the liquid phase of the reaction medium.

Agitation of the reaction medium undergoing liquid-phase oxidation is frequently provided by mechanical agitation means in vessels such as, for example, continuous stirred tank reactors ("CSTRs"). Although CSTRs can provide thorough mixing of the reaction medium, CSTRs have a number of drawbacks. For example, CSTRs have a relatively high capital cost due to their requirement for expensive motors, fluid-sealed bearings and drive shafts, and/or complex stirring mechanisms. Further, the rotating and/or oscillating mechanical components of conventional CSTRs require regular maintenance. The labor and shutdown time associated with such maintenance adds to the operating cost of CSTRs. However, even with regular maintenance, the mechanical agitation systems employed in CSTRs are prone to mechanical failure and may require replacement over relatively short periods of time.

Bubble column reactors provide an attractive alternative to CSTRs and other mechanically agitated oxidation reactors. Bubble column reactors provide agitation of the reaction medium without requiring expensive and unreliable mechanical equipment. Bubble column reactors typically include an elongated upright reaction zone within which the reaction medium is contained. Agitation of the reaction medium in the reaction zone is provided primarily by the natural buoyancy of gas bubbles rising through the liquid phase of the reaction medium. This natural-buoyancy agitation provided in bubble column reactors reduces capital and maintenance costs relative to mechanically agitated reactors. Further, the substantial absence of moving mechanical parts associated with bubble column reactors provides an oxidation system that is less prone to mechanical failure than mechanically agitated reactors.

When liquid-phase partial oxidation of para-xylene is carried out in a conventional oxidation reactor (CSTR or bubble column), the product withdrawn from the reactor is typically a slurry comprising crude terephthalic acid ("CTA") and a mother liquor. CTA contains relatively high levels of impurities (e.g., 4-carboxybenzaldehyde, para-toluic acid, fluorenones, and other color bodies) that render it unsuitable as a feedstock for the production of PET. Thus, the CTA produced in conventional oxidation reactors is typically subjected to a purification process that converts the CTA into purified terephthalic acid ("PTA") suitable for making PET.

Although advances have been made in the art of liquid-phase oxidation reactions, improvements are still needed.

SUMMARY OF THE INVENTION

One embodiment of the present invention concerns a system for producing a polycarboxylic acid by contacting a slurry with a gas-phase oxidant. The system of this embodiment comprises a primary oxidation reactor comprising a first slurry outlet, and a secondary oxidation reactor comprising a slurry inlet and a second slurry outlet. In this embodiment, the slurry inlet is in downstream fluid-flow communication with the first slurry outlet; the secondary oxidation reactor defines therein a secondary reaction zone having a maximum length $L_S$ and a maximum diameter $D_S$, and the slurry inlet is spaced from the bottom of the secondary reaction zone by a distance in the range of from about 0.3 $L_S$ to about 0.9 $L_S$.

Another embodiment of the present invention concerns a method for making a polycarboxylic acid composition. The method of this embodiment comprises (a) subjecting a first multi-phase reaction medium comprising an oxidizable compound to oxidation in a primary reaction zone defined in a primary oxidation reactor to thereby produce a first slurry; and (b) contacting at least a portion of the first slurry with a gas-phase oxidant in a secondary reaction zone defined in a secondary oxidation reactor to thereby produce a second slurry. In this embodiment, the secondary reaction zone has a maximum length $L_S$ and a maximum diameter $D_S$, and at least a portion of the first slurry is introduced into the secondary reaction zone at a slurry inlet region spaced from the bottom of the secondary reaction zone by a distance in the range of from about 0.3 $L_S$ to about 0.9 $L_S$.

BRIEF DESCRIPTION OF THE DRAWINGS

Embodiments of the invention are described in detail below with reference to the attached drawing figures, wherein:

FIG. 2 is a side view of a bubble column reactor equipped with an external secondary oxidation reactor that receives a slurry from a sidedraw in the primary oxidation reactor;

FIG. 3 is an expanded sectional bottom view of the sidedraw reactor taken along line 3-3 in FIG. 2, particularly illustrating the location and configuration of an upper oxidant sparger used to introduce at least a portion of an oxidant stream into the reactor;

DETAILED DESCRIPTION

Various embodiments of the present invention concern the liquid-phase partial oxidation of an oxidizable compound. Such oxidation can be carried out in the liquid phase of a multi-phase reaction medium contained in one or more agitated reactors. Suitable agitated reactors include, for example, bubble-agitated reactors (e.g., bubble column reactors), mechanically agitated reactors (e.g., continuous stirred tank reactors), and flow agitated reactors (e.g., jet reactors). In one or more embodiments, the liquid-phase oxidation can be carried out using at least one bubble column reactor.

As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the term "agitation" shall denote work dissipated into the reaction medium causing fluid flow and/or mixing. As used herein, the terms "majority," "primarily," and "predominately" shall mean more than 50 percent. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. As used herein, the term "flow agitation" shall denote agitation of the reaction medium caused by high velocity injection and/or recirculation of one or more fluids in the reaction medium. For example, flow agitation can be provided by nozzles, ejectors, and/or eductors.

In various embodiments, the portion of the agitation of the reaction medium in the bubble column reactor during oxidation provided by mechanical and/or flow agitation can be less than about 40 percent, less than about 20 percent, or less than 5 percent. Additionally, the amount of mechanical and/or flow agitation imparted to the multi-phase reaction medium during oxidation can be less than about 3 kilowatts per cubic meter of the reaction medium, less than about 2 kilowatts per cubic meter, or less than 1 kilowatt per cubic meter.

Figure 1:
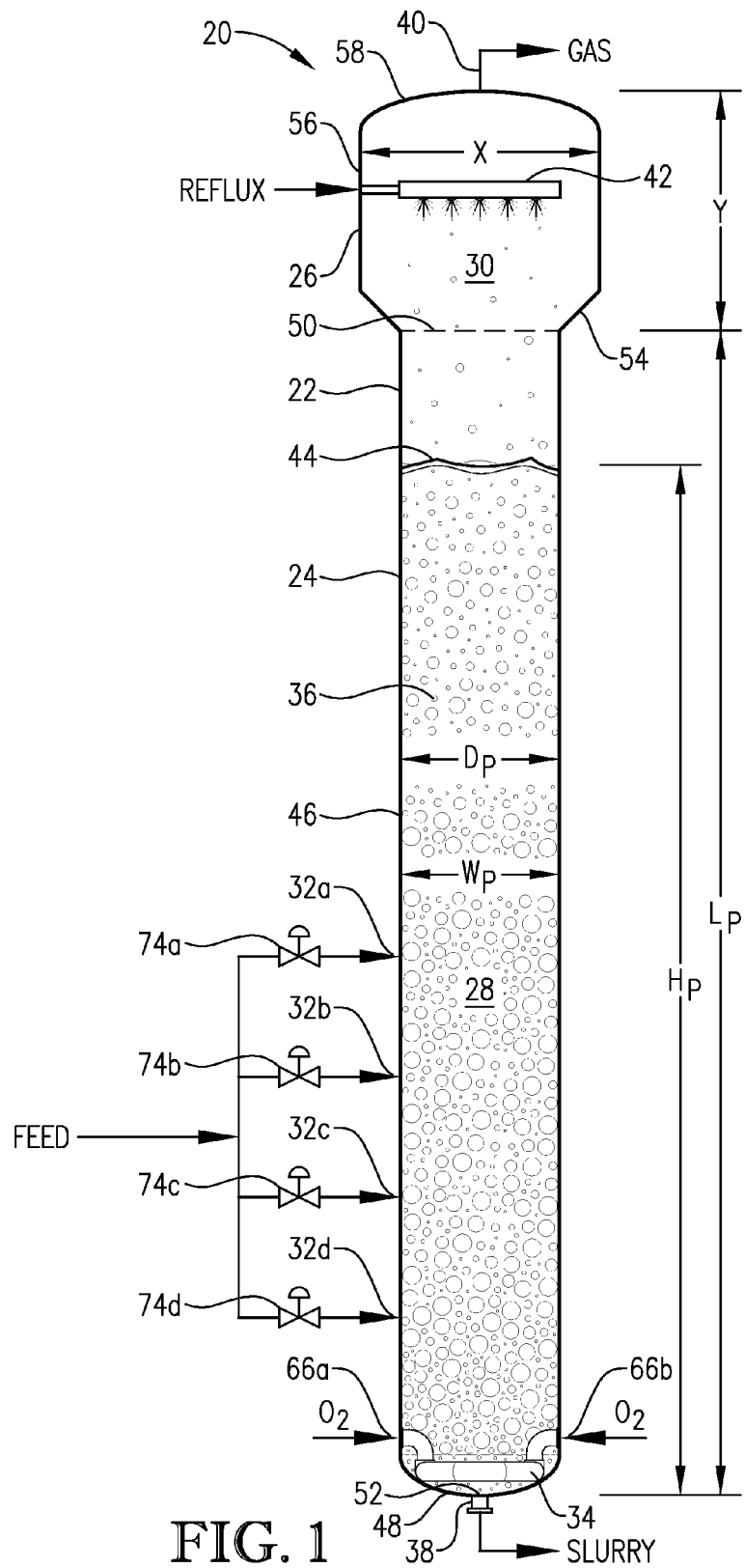
FIG. 1 is a side view of an oxidation reactor constructed in accordance with one embodiment of the present invention, particularly illustrating the introduction of feed, oxidant, and reflux streams into the reactor, the presence of a multi-phase reaction medium in the reactor, and the withdrawal of a gas and a slurry from the top and bottom of the reactor, respectively.

Referring now to FIG. 1, a bubble column reactor 20 is illustrated as comprising a vessel shell 22 having a reaction section 24 and a disengagement section 26. Reaction section 24 defines a reaction zone 28, while disengagement section 26 defines a disengagement zone 30. A predominately liquid-phase feed stream can be introduced into reaction zone 28 via feed inlets 32a,b,c,d. A predominately gas-phase oxidant stream can be introduced into reaction zone 28 via an oxidant sparger 34 located in the lower portion of reaction zone 28. The liquid-phase feed stream and gas-phase oxidant stream cooperatively form a multi-phase reaction medium 36 within reaction zone 28. In various embodiments, multi-phase reaction medium 36 can comprise a liquid phase and a gas phase. In other various embodiments, multiphase reaction medium 36 can comprise a three-phase medium having solid-phase, liquid-phase, and gas-phase components. The solid-phase component of the reaction medium 36 can precipitate within reaction zone 28 as a result of the oxidation reaction carried out in the liquid phase of reaction medium 36. Bubble column reactor 20 includes a slurry outlet 38 located near the bottom of reaction zone 28 and a gas outlet 40 located near the top of disengagement zone 30. A slurry effluent comprising liquid-phase and solid-phase components of reaction medium 36 can be withdrawn from reaction zone 28 via slurry outlet 38, while a predominantly gaseous effluent can be withdrawn from disengagement zone 30 via gas outlet 40.

The liquid-phase feed stream introduced into bubble column reactor 20 via feed inlets 32a,b,c,d can comprise an oxidizable compound, a solvent, and a catalyst system.

The oxidizable compound present in the liquid-phase feed stream can comprise at least one hydrocarbyl group. In various embodiments, the oxidizable compound can be an aromatic compound. Furthermore, the oxidizable compound can be an aromatic compound with at least one attached hydrocarbyl group or at least one attached substituted hydrocarbyl group or at least one attached heteroatom or at least one attached carboxylic acid function (—COOH). In one or more embodiments, the oxidizable compound can be an aromatic compound with at least one attached hydrocarbyl group or at least one attached substituted hydrocarbyl group with each attached group comprising from 1 to 5 carbon atoms. Additionally, the oxidizable compound can be an aromatic compound having exactly two attached groups with each attached group comprising exactly one carbon atom and consisting of methyl groups and/or substituted methyl groups and/or at most one carboxylic acid group. Examples of suitable compounds for use as the oxidizable compound include, but are not limited to, para-xylene, meta-xylene, para-tolualdehyde, meta-tolualdehyde, para-toluic acid, meta-toluic acid, and/or acetaldehyde. In one or more embodiments, the oxidizable compound is para-xylene.

A "hydrocarbyl group," as defined herein, is at least one carbon atom that is bonded only to hydrogen atoms or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. Aromatic compounds, as defined herein, comprise an aromatic ring. Such aromatic compounds can have at least 6 carbon atoms and, in various embodiments, can have only carbon atoms as part of the ring. Suitable examples of such aromatic rings include, but are not limited to, benzene, biphenyl, terphenyl, naphthalene, and other carbon-based fused aromatic rings.

If the oxidizable compound present in the liquid-phase feed stream is a normally-solid compound (i.e., is a solid at standard temperature and pressure), the oxidizable compound can be substantially dissolved in the solvent when introduced into reaction zone 28. The boiling point of the oxidizable compound at atmospheric pressure can be at least about 50° C., in the range of from about 80 to about 400° C., or in the range of from 125 to 155° C. The amount of oxidizable compound present in the liquid-phase feed can be in the range of from about 2 to about 40 weight percent, in the range of from about 4 to about 20 weight percent, or in the range of from 6 to 15 weight percent.

It is now noted that the oxidizable compound present in the liquid-phase feed may comprise a combination of two or more different oxidizable chemicals. These two or more different chemical materials can be fed commingled in the liquid-phase feed stream or may be fed separately in multiple feed streams. For example, an oxidizable compound comprising para-xylene, meta-xylene, para-tolualdehyde, para-toluic acid, and acetaldehyde may be fed to the reactor via a single inlet or multiple separate inlets.

The solvent present in the liquid-phase feed stream can comprise an acid component and a water component. The solvent can be present in the liquid-phase feed stream at a concentration in the range of from about 60 to about 98 weight percent, in the range of from about 80 to about 96 weight percent, or in the range of from 85 to 94 weight percent. The acid component of the solvent can be primarily an organic low molecular weight monocarboxylic acid having 1-6 carbon atoms, or 2 carbon atoms. In various embodiments, the acid component of the solvent can primarily be acetic acid. The acid component can make up at least about 75 weight percent of the solvent, at least about 80 weight percent of the solvent, or in the range of from 85 to 98 weight percent of the solvent, with the balance being water or primarily water. The solvent introduced into bubble column reactor 20 can include small quantities of impurities such as, for example, para-tolualdehyde, terephthaldehyde, 4-carboxybenzaldehyde ("4-CBA"), benzoic acid, para-toluic acid, para-toluic aldehyde, alpha-bromo-para-toluic acid, isophthalic acid, phthalic acid, trimellitic acid, polyaromatics, and/or suspended particulate. In various embodiments, the total amount of impurities in the solvent introduced into bubble column reactor 20 can be less than about 3 weight percent.

The catalyst system present in the liquid-phase feed stream can be a homogeneous, liquid-phase catalyst system capable of promoting oxidation (including partial oxidation) of the oxidizable compound. In various embodiments, the catalyst system can comprise at least one multivalent transition metal. In one or more embodiments, the multivalent transition metal can comprise cobalt. Additionally, the catalyst system can comprise cobalt and bromine. Furthermore, the catalyst system can comprise cobalt, bromine, and manganese.

When cobalt is present in the catalyst system, the amount of cobalt present in the liquid-phase feed stream can be such that the concentration of cobalt in the liquid phase of reaction medium 36 is maintained in the range of from about 300 to about 6,000 parts per million by weight ("ppmw"), in the range of from about 700 to about 4,200 ppmw, or in the range of from 1,200 to 3,000 ppmw. When bromine is present in the catalyst system, the amount of bromine present in the liquid-phase feed stream can be such that the concentration of bromine in the liquid phase of reaction medium 36 is maintained in the range of from about 300 to about 5,000 ppmw, in the range of from about 600 to about 4,000 ppmw, or in the range of from 900 to 3,000 ppmw. When manganese is present in the catalyst system, the amount of manganese present in the liquid-phase feed stream can be such that the concentration of manganese in the liquid phase of reaction medium 36 is maintained in the range of from about 20 to about 1,000 ppmw, in the range of from about 40 to about 500 ppmw, or in the range of from 50 to 200 ppmw.

The concentrations of the cobalt, bromine, and/or manganese in the liquid phase of reaction medium 36, provided above, are expressed on a time-averaged and volume-averaged basis. As used herein, the term "time-averaged" shall denote an average of at least 10 measurements taken equally over a continuous period of at least 100 seconds. As used herein, the term "volume-averaged" shall denote an average of at least 10 measurements taken at uniform 3-dimensional spacing throughout a certain volume.

The weight ratio of cobalt to bromine (Co:Br) in the catalyst system introduced into reaction zone 28 can be in the range of from about 0.25:1 to about 4:1, in the range of from about 0.5:1 to about 3:1, or in the range of from 0.75:1 to 2:1. The weight ratio of cobalt to manganese (Co:Mn) in the catalyst system introduced into reaction zone 28 can be in the range of from about 0.3:1 to about 40:1, in the range of from about 5:1 to about 30:1, or in the range of from 10:1 to 25:1.

The liquid-phase feed stream introduced into bubble column reactor 20 can include small quantities of impurities such as, for example, toluene, ethylbenzene, para-tolualdehyde, terephthaldehyde, 4-CBA, benzoic acid, para-toluic acid, para-toluic aldehyde, alpha-bromo-para-toluic acid, isophthalic acid, phthalic acid, trimellitic acid, polyaromatics, and/or suspended particulate. When bubble column reactor 20 is employed for the production of terephthalic acid, meta-xylene and ortho-xylene are also considered impurities. In various embodiments, the total amount of impurities in the liquid-phase feed stream introduced into bubble column reactor 20 can be less than about 3 weight percent.

Although FIG. 1 illustrates an embodiment where the oxidizable compound, the solvent, and the catalyst system are mixed together and introduced into bubble column reactor 20 as a single feed stream, in an alternative embodiment, the oxidizable compound, the solvent, and the catalyst can be separately introduced into bubble column reactor 20. For example, it is possible to feed a pure para-xylene stream into bubble column reactor 20 via an inlet separate from the solvent and catalyst inlet(s).

The predominately gas-phase oxidant stream introduced into bubble column reactor 20 via oxidant sparger 34 comprises molecular oxygen ($O_2$). In various embodiments, the oxidant stream comprises in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gasses, such as nitrogen, that are inert to oxidation. In one or more embodiments, the oxidant stream can consist essentially of molecular oxygen and nitrogen. In various embodiments, the oxidant stream can be dry air that comprises about 21 mole percent molecular oxygen and about 78 to about 81 mole percent nitrogen. In other embodiments, the gas-phase oxidant can be enriched air, and can comprise 25 mole percent, 30 mole percent, 35 mole percent, 40 mole percent, 50 mole percent, 55 mole percent, 60 mole percent, 70 mole percent, or 80 mole percent molecular oxygen. In still other embodiments, the oxidant stream can comprise substantially pure oxygen.

Referring still to FIG. 1, bubble column reactor 20 can be equipped with a reflux distributor 42 positioned above an upper surface 44 of reaction medium 36. Reflux distributor 42 is operable to introduce droplets of a predominately liquid-phase reflux stream into disengagement zone 30 by any means of droplet formation known in the art. In various embodiments, reflux distributor 42 can produce a spray of droplets directed downwardly towards upper surface 44 of reaction medium 36. This downward spray of droplets can affect (i.e., engage and influence) at least about 50 percent, at least about 75 percent, or at least 90 percent of the maximum horizontal cross-sectional area of disengagement zone 30. This downward liquid reflux spray can help prevent foaming at or above upper surface 44 of reaction medium 36 and can also aid in the disengagement of any liquid or slurry droplets entrained in the upwardly moving gas that flows towards gas outlet 40. Further, the liquid reflux may serve to reduce the amount of particulates and potentially precipitating compounds (e.g., dissolved benzoic acid, para-toluic acid, 4-CBA, terephthalic acid, and catalyst metal salts) exiting in the gaseous effluent withdrawn from disengagement zone 30 via gas outlet 40. In addition, the introduction of reflux droplets into disengagement zone 30 can, by a distillation action, be used to adjust the composition of the gaseous effluent withdrawn via gas outlet 40.

The liquid reflux stream introduced into bubble column reactor 20 via reflux distributor 42 can have the same or about the same composition as the solvent component of the liquid-phase feed stream introduced into bubble column reactor 20 via feed inlets 32a,b,c,d. Thus, the liquid reflux stream can comprise an acid component and water. The acid component of the reflux stream can be a low molecular weight organic monocarboxylic acid having 1-6 carbon atoms, or 2 carbon atoms. In various embodiments, the acid component of the reflux stream can be acetic acid. Furthermore, the acid component can make up at least about 75 weight percent of the reflux stream, at least about 80 weight percent of the reflux stream, or in the range of from 85 to 98 weight percent of the reflux stream, with the balance being water or primarily water. Because the reflux stream typically can have the same or substantially the same composition as the solvent in the liquid-phase feed stream, when this description refers to the "total solvent" introduced into the reactor, such "total solvent" shall include both the reflux stream and the solvent portion of the feed stream.

During liquid-phase oxidation in bubble column reactor 20, the feed, oxidant, and reflux streams can be substantially continuously introduced into reaction zone 28, while the gas and slurry effluent streams are substantially continuously withdrawn from reaction zone 28. As used herein, the term "substantially continuously" shall mean for a period of at least 10 hours interrupted by less than 10 minutes. During oxidation, the oxidizable compound (e.g., para-xylene) can be substantially continuously introduced into reaction zone 28 at a rate of at least about 8,000 kilograms per hour, at a rate in the range of from about 15,000 to about 200,000 kilograms per hour, in the range of from about 22,000 to about 150,000 kilograms per hour, or in the range of from 30,000 to 100,000 kilograms per hour. Although the flow rates of the incoming feed, oxidant, and reflux streams can be substantially steady, it is now noted that one embodiment contemplates pulsing the incoming feed, oxidant, and/or reflux streams in order to improve mixing and mass transfer. When the incoming feed, oxidant, and/or reflux streams are introduced in a pulsed fashion, their flow rates can vary within about 0 to about 500 percent of the steady-state flow rates recited herein, within about 30 to about 200 percent of the steady-state flow rates recited herein, or within 80 to 120 percent of the steady-state flow rates recited herein.

The average space-time rate of reaction ("STR") in bubble column oxidation reactor 20 is defined as the mass of the oxidizable compound fed per unit volume of reaction medium 36 per unit time (e.g., kilograms of para-xylene fed per cubic meter per hour). In conventional usage, the amount of oxidizable compound not converted to product would typically be subtracted from the amount of oxidizable compound in the feed stream before calculating the STR. However, conversions and yields are typically high for many of the oxidizable compounds referred to herein (e.g., para-xylene), and it is convenient to define the term herein as stated above. For reasons of capital cost and operating inventory, among others, the reaction can be conducted with a high STR. However, conducting the reaction at increasingly higher STR may affect the quality or yield of the partial oxidation. Bubble column reactor 20 may be particularly useful when the STR of the oxidizable compound (e.g., para-xylene) is in the range of from about 25 kilograms per cubic meter per hour ("kg/$m^3$/hr.") to about 400 kg/$m^3$/hr., in the range of from about 30 kg/$m^3$/hr. to about 250 kg/$m^3$/hr., in the range of from about 35 kg/$m^3$/hr. to about 150 kg/$m^3$/hr., or in the range of from 40 kg/$m^3$/hr. to 100 kg/$m^3$/hr.

The oxygen-STR in bubble column oxidation reactor 20 is defined as the weight of molecular oxygen consumed per unit volume of reaction medium 36 per unit time (e.g., kilograms of molecular oxygen consumed per cubic meter per hour). For reasons of capital cost and oxidative consumption of solvent, among others, the reaction can be conducted with a high oxygen-STR. However, conducting the reaction at increasingly higher oxygen-STR eventually reduces the quality or yield of the partial oxidation. Without being bound by theory, it appears that this possibly relates to the transfer rate of molecular oxygen from the gas phase into the liquid at the interfacial surface area and thence into the bulk liquid. Too high an oxygen-STR possibly leads to too low a dissolved oxygen content in the bulk liquid phase of the reaction medium.

The global-average-oxygen-STR is defined herein as the weight of all oxygen consumed in the entire volume of reaction medium 36 per unit time (e.g., kilograms of molecular oxygen consumed per cubic meter per hour). Bubble column reactor 20 may be particularly useful when the global-average-oxygen-STR is in the range of from about 25 kg/$m^3$/hr. to about 400 kg/$m^3$/hr., in the range of from about 30 kg/$m^3$/hr.

to about 250 kg/m³/hr., in the range of from about 35 kg/m³/hr. to about 150 kg/m³/hr., or in the range of from 40 kg/m³/hr. to 100 kg/m³/hr.

During oxidation in bubble column reactor 20, the ratio of the mass flow rate of the total solvent (from both the feed and reflux streams) to the mass flow rate of the oxidizable compound entering reaction zone 28 can be maintained in the range of from about 2:1 to about 50:1, in the range of from about 5:1 to about 40:1, or in the range of from 7.5:1 to 25:1. In various embodiments, the ratio of the mass flow rate of solvent introduced as part of the feed stream to the mass flow rate of solvent introduced as part of the reflux stream can be maintained in the range of from about 0.5:1 to no reflux stream flow whatsoever, in the range of from about 0.5:1 to about 4:1, in the range of from about 1:1 to about 2:1, or in the range of from 1.25:1 to 1.5:1.

During liquid-phase oxidation in bubble column reactor 20, the oxidant stream can be introduced into bubble column reactor 20 in an amount that provides molecular oxygen somewhat exceeding the stoichiometric oxygen demand. The amount of excess molecular oxygen required for best results with a particular oxidizable compound affects the overall economics of the liquid-phase oxidation. During liquid-phase oxidation in bubble column reactor 20, the ratio of the mass flow rate of the oxidant stream to the mass flow rate of the oxidizable organic compound (e.g., para-xylene) entering reactor 20 can be maintained in the range of from about 0.5:1 to about 20:1, in the range of from about 1:1 to about 10:1, or in the range of from 2:1 to 6:1.

Referring still to FIG. 1, the feed, oxidant, and reflux streams introduced into bubble column reactor 20 can cooperatively form at least a portion of multi-phase reaction medium 36. Reaction medium 36 can be a three-phase medium comprising a solid phase, a liquid phase, and a gas phase. As mentioned above, oxidation of the oxidizable compound (e.g., para-xylene) can take place predominately in the liquid phase of reaction medium 36. Thus, the liquid phase of reaction medium 36 can comprise dissolved oxygen and the oxidizable compound. The exothermic nature of the oxidation reaction that takes place in bubble column reactor 20 can cause a portion of the solvent (e.g., acetic acid and water) introduced via feed inlets 32*a,b,c,d* to boil/vaporize. Thus, the gas phase of reaction medium 36 in reactor 20 can be formed primarily of vaporized solvent and an undissolved, unreacted portion of the oxidant stream.

Certain prior art oxidation reactors employ heat exchange tubes/fins to heat or cool the reaction medium. However, such heat exchange structures may be undesirable in the inventive reactor and process described herein. Thus, in various embodiments, bubble column reactor 20 can be designed to include substantially no surfaces that contact reaction medium 36 and exhibit a time-averaged heat flux greater than 30,000 watts per meter squared. In addition, in various embodiments, less than about 50 percent, less than about 30 percent, or less than 10 percent of the time-averaged heat of reaction of reaction medium 36 is be removed by heat exchange surfaces.

The concentration of dissolved oxygen in the liquid phase of reaction medium 36 is a dynamic balance between the rate of mass transfer from the gas phase and the rate of reactive consumption within the liquid phase (i.e., it is not set simply by the partial pressure of molecular oxygen in the supplying gas phase, though this is one factor in the supply rate of dissolved oxygen and it does affect the limiting upper concentration of dissolved oxygen). The amount of dissolved oxygen varies locally, being higher near bubble interfaces. Globally, the amount of dissolved oxygen depends on the balance of supply and demand factors in different regions of reaction medium 36. Temporally, the amount of dissolved oxygen depends on the uniformity of gas and liquid mixing relative to chemical consumption rates. In designing to match appropriately the supply of and demand for dissolved oxygen in the liquid phase of reaction medium 36, the time-averaged and volume-averaged oxygen concentration in the liquid phase of reaction medium 36 can be maintained above about 1 ppm molar, in the range from about 4 to about 1,000 ppm molar, in the range from about 8 to about 500 ppm molar, or in the range from 12 to 120 ppm molar.

The liquid-phase oxidation reaction carried out in bubble column reactor 20 can be a precipitating reaction that generates solids. In various embodiments, the liquid-phase oxidation carried out in bubble column reactor 20 can cause at least about 10 weight percent, at least about 50 weight percent, or at least 90 weight percent of the oxidizable compound (e.g., para-xylene) introduced into reaction zone 28 to form a solid compound (e.g., crude terephthalic acid particles) in reaction medium 36. In one or more embodiments, the total amount of solids in reaction medium 36 can be greater than about 3 weight percent, in the range of from about 5 to about 40 weight percent, in the range of from about 10 to about 35 weight percent, or in the range of from 15 to 30 weight percent, on a time-averaged and volume-averaged basis. In various embodiments, a substantial portion of the oxidation product (e.g., terephthalic acid) produced in bubble column reactor 20 can be present in reaction medium 36 as solids, as opposed to remaining dissolved in the liquid phase of reaction medium 36. The amount of the solid phase oxidation product present in reaction medium 36 can be at least about 25 percent by weight of the total oxidation product (solid and liquid phase) in reaction medium 36, at least about 75 percent by weight of the total oxidation product in reaction medium 36, or at least 95 percent by weight of the total oxidation product in reaction medium 36. The numerical ranges provided above for the amount of solids in reaction medium 36 apply to substantially steady-state operation of bubble column 20 over a substantially continuous period of time, not to start-up, shut-down, or sub-optimal operation of bubble column reactor 20. The amount of solids in reaction medium 36 is determined by a gravimetric method. In this gravimetric method, a representative portion of slurry is withdrawn from the reaction medium and weighed. At conditions that effectively maintain the overall solid-liquid partitioning present within the reaction medium, free liquid is removed from the solids portion by sedimentation or filtration, effectively without loss of precipitated solids and with less than about 10 percent of the initial liquid mass remaining with the portion of solids. The remaining liquid on the solids is evaporated to dryness, effectively without sublimation of solids. The remaining portion of solids is weighed. The ratio of the weight of the portion of solids to the weight of the original portion of slurry is the fraction of solids, typically expressed as a percentage.

The precipitating reaction carried out in bubble column reactor 20 can cause fouling (i.e., solids build-up) on the surface of certain rigid structures that contact reaction medium 36. Thus, in one embodiment, bubble column reactor 20 may be designed to include substantially no internal heat exchange, stiffing, or baffling structures in reaction zone 28 because such structures would be prone to fouling. If internal structures are present in reaction zone 28, it is desirable to avoid internal structures having outer surfaces that include a significant amount of upwardly facing planar surface area because such upwardly facing planar surfaces would be highly prone to fouling. Thus, if any internal structures are present in reaction zone 28, less than about 20 percent of the total upwardly facing exposed outer surface area of such internal structures should be formed by substantially planar surfaces inclined less than about 15 degrees from horizontal. Internal structures with this type of configuration are referred to herein as having a "non-fouling" configuration.

Referring again to FIG. 1, the physical configuration of bubble column reactor 20 helps provide for optimized oxidation of the oxidizable compound (e.g., para-xylene) with minimal impurity generation. In various embodiments, elongated reaction section 24 of vessel shell 22 can include a substantially cylindrical main body 46 and a lower head 48. The upper end of reaction zone 28 is defined by a horizontal plane 50 extending across the top of cylindrical main body 46. A lower end 52 of reaction zone 28 is defined by the lowest internal surface of lower head 48. Typically, lower end 52 of reaction zone 28 is located proximate the opening for slurry outlet 38. Thus, elongated reaction zone 28 defined within bubble column reactor 20 has a maximum length "$L_p$" measured from the top end 50 to the bottom end 52 of reaction zone 28 along the axis of elongation of cylindrical main body 46. The length "$L_p$" of reaction zone 28 can be in the range of from about 10 to about 100 meters, in the range of from about 20 to about 75 meters, or in the range of from 25 to 50 meters. Reaction zone 28 has a maximum diameter (width) "$D_p$" that is typically equal to the maximum internal diameter of cylindrical main body 46. The maximum diameter $D_p$ of reaction zone 28 can be in the range of from about 1 to about 12 meters, in the range of from about 2 to about 10 meters, in the range of from about 3.1 to about 9 meters, or in the range of from 4 to 8 meters. In one or more embodiments, reaction zone 28 can have a length-to-diameter "$L_p:D_p$" ratio in the range of from about 6:1 to about 30:1, in the range of from about 8:1 to about 20:1, or in the range of from 9:1 to 15:1.

As discussed above, reaction zone 28 of bubble column reactor 20 receives multi-phase reaction medium 36. Reaction medium 36 has a bottom end coincident with lower end 52 of reaction zone 28 and a top end located at upper surface 44. Upper surface 44 of reaction medium 36 is defined along a horizontal plane that cuts through reaction zone 28 at a vertical location where the contents of reaction zone 28 transitions from a gas-phase-continuous state to a liquid-phase-continuous state. Upper surface 44 can be positioned at the vertical location where the local time-averaged gas hold-up of a thin horizontal slice of the contents of reaction zone 28 is 0.9.

Reaction medium 36 has a maximum height "$H_p$" measured between its upper and lower ends. The maximum width "$W_p$" of reaction medium 36 is typically equal to the maximum diameter "$D_p$" of cylindrical main body 46. During liquid-phase oxidation in bubble column reactor 20, $H_p$ can be maintained at about 60 to about 120 percent of $L_p$, about 80 to about 110 percent of $L_p$, or 85 to 100 percent of $L_p$. In various embodiments, reaction medium 36 can have a height-to-width "$H_p:W_p$" ratio greater than about 3:1, in the range of from about 7:1 to about 25:1, in the range of from about 8:1 to about 20:1, or in the range of from 9:1 to 15:1. In one embodiment of the invention, $L_p=H_p$ and $D_p=W_p$ so that various dimensions or ratios provide herein for $L_p$ and $D_p$ also apply to $H_p$ and $W_p$, and vice-versa.

The relatively high $L_p:D_p$ and $H_p:W_p$ ratios provided in accordance with an embodiment of the invention can contribute to several important advantages of the inventive system. As discussed in further detail below, it has been discovered that higher $L_p:D_p$ and $H_p:W_p$ ratios, as well as certain other features discussed below, can promote beneficial vertical gradients in the concentrations of molecular oxygen and/or the oxidizable compound (e.g., para-xylene) in reaction medium 36. Contrary to conventional wisdom, which would favor a well-mixed reaction medium with relatively uniform concentrations throughout, it has been discovered that the vertical staging of the oxygen and/or the oxidizable compound concentrations facilitate a more effective and economical oxidation reaction. Minimizing the oxygen and oxidizable compound concentrations near the top of reaction medium 36 can help avoid loss of unreacted oxygen and unreacted oxidizable compound through upper gas outlet 40. However, if the concentrations of oxidizable compound and unreacted oxygen are low throughout reaction medium 36, then the rate and/or selectivity of oxidation are reduced. Thus, in various embodiments, the concentrations of molecular oxygen and/or the oxidizable compound can be significantly higher near the bottom of reaction medium 36 than near the top of reaction medium 36.

In addition, high $L_p:D_p$ and $H_p:W_p$ ratios can cause the pressure at the bottom of reaction medium 36 to be substantially greater than the pressure at the top of reaction medium 36. This vertical pressure gradient is a result of the height and density of reaction medium 36. One advantage of this vertical pressure gradient is that the elevated pressure at the bottom of the vessel drives more oxygen solubility and mass transfer than would otherwise be achievable at comparable temperatures and overhead pressures in shallow reactors. Thus, the oxidation reaction can be carried out at lower temperatures than would be required in a shallower vessel. When bubble column reactor 20 is used for the partial oxidation of para-xylene to crude terephthalic acid (CTA), the ability to operate at lower reaction temperatures with the same or better oxygen mass transfer rates has a number of advantages. For example, low temperature oxidation of para-xylene reduces the amount of solvent burned during the reaction. As discussed in further detail below, low temperature oxidation also favors the formation of small, high surface area, loosely bound, easily dissolved CTA particles, which can be subjected to more economical purification techniques than the large, low surface area, dense CTA particles produced by conventional high temperature oxidation processes.

During oxidation in reactor 20, the time-averaged and volume-averaged temperature of reaction medium 36 can be maintained in the range of from about 125 to about 200° C., in the range of from about 140 to about 180° C., or in the range of from 150 to 170° C. The overhead pressure above reaction medium 36 can be maintained in the range of from about 1 to about 20 bar gauge ("barg"), in the range of from about 2 to about 12 barg, or in the range of from 4 to 8 barg. The pressure difference between the top of reaction medium 36 and the bottom of reaction medium 36 can be in the range of from about 0.4 to about 5 bar, in the range of from about 0.7 to about 3 bar, or in the range of from 1 to 2 bar. Although the overhead pressure above reaction medium 36 can generally be maintained at a relatively constant value, one embodiment contemplates pulsing the overhead pressure to facilitate improved mixing and/or mass transfer in reaction medium 36. When the overhead pressure is pulsed, the pulsed pressures can range between about 60 to about 140 percent, between about 85 and about 115 percent, or between 95 and 105 percent of the steady-state overhead pressure recited herein.

A further advantage of the high $L_p:D_p$ ratio of reaction zone 28 is that it can contribute to an increase in the average superficial velocity of reaction medium 36. The term "superficial velocity" and "superficial gas velocity," as used herein with reference to reaction medium 36, shall denote the volumetric flow rate of the gas phase of reaction medium 36 at an elevation in the reactor divided by the horizontal cross-sectional area of the reactor at that elevation. The increased superficial velocity provided by the high $L_p:D_p$ ratio of reaction zone 28 can promote local mixing and increase the gas hold-up of reaction medium 36. The time-averaged superficial velocities of reaction medium 36 at one-quarter height, half height, and/or three-quarter height of reaction medium 36 can be greater than about 0.3 meters per second, in the range of from about 0.8 to about 5 meters per second, in the range of from about 0.9 to about 4 meters per second, or in the range of from 1 to 3 meters per second.

Referring still to FIG. 1, disengagement section 26 of bubble column reactor 20 can simply be a widened portion of vessel shell 22 located immediately above reaction section 24. Disengagement section 26 reduces the velocity of the upwardly-flowing gas phase in bubble column reactor 20 as the gas phase rises above the upper surface 44 of reaction medium 36 and approaches gas outlet 40. This reduction in the upward velocity of the gas phase helps facilitate removal of entrained liquids and/or solids in the upwardly flowing gas phase and thereby reduces undesirable loss of certain components present in the liquid phase of reaction medium 36.

Disengagement section 26 can include a generally frusto-conical transition wall 54, a generally cylindrical broad sidewall 56, and an upper head 58. The narrow lower end of transition wall 54 is coupled to the top of cylindrical main body 46 of reaction section 24. The wide upper end of transition wall 54 is coupled to the bottom of broad sidewall 56. Transition wall 54 can extend upwardly and outwardly from its narrow lower end at an angle in the range of from about 10 to about 70 degrees from vertical, in the range of about 15 to about 50 degrees from vertical, or in the range of from 15 to 45 degrees from vertical. Broad sidewall 56 has a maximum diameter "X" that is generally greater than the maximum diameter $D_p$ of reaction section 24, though when the upper portion of reaction section 24 has a smaller diameter than the overall maximum diameter of reaction section 24, then X may actually be smaller than $D_p$. In various embodiments, the ratio of the diameter of broad sidewall 56 to the maximum diameter of reaction section 24 "$X:D_p$" can be in the range of from about 0.8:1 to about 4:1, or in the range of from 1.1:1 to 2:1. Upper head 58 is coupled to the top of broad sidewall 56. Upper head 58 can be a generally elliptical head member defining a central opening that permits gas to escape disengagement zone 30 via gas outlet 40. Alternatively, upper head 58 may be of any shape, including conical. Disengagement zone 30 has a maximum height "Y" measured from the top 50 of reaction zone 28 to the upper-most portion of disengagement zone 30. The ratio of the length of reaction zone 28 to the height of disengagement zone 30 "$L_p:Y$" can be in the range of from about 2:1 to about 24:1, in the range of from about 3:1 to about 20:1, or in the range of from 4:1 to 16:1.

Referring still to FIG. 1, during operation a gas-phase oxidant (e.g., air) can be introduced into reaction zone 28 via oxidant inlets 66a,b and oxidant sparger 34. Oxidant sparger 34 can have any shape or configuration that permits passage of the gas-phase oxidant into reaction zone 28. For instance, oxidant sparger 34 can comprise a circular or polygonal (e.g., octagonal) ring member defining a plurality of oxidant discharge openings. In various embodiments, some or all of the oxidant discharge openings can be configured to discharge the gas-phase oxidant in a generally downward direction. Regardless of the specific configuration of oxidant sparger 34, the oxidant sparger can be physically configured and operated in a manner that minimizes the pressure drop associated with discharging the oxidant stream through the oxidant discharge openings and into the reaction zone. Such pressure drop is calculated as the time-averaged static pressure of the oxidant stream inside the flow conduit at oxidant inlets 66a,b of the oxidant sparger minus the time-averaged static pressure in the reaction zone at the elevation where one-half of the oxidant stream is introduced above that vertical location and one-half of the oxidant stream is introduced below that vertical location. In various embodiments, the time-averaged pressure drop associated with discharging the oxidant stream from the oxidant sparger 34 can be less than about 0.3 megapascal ("MPa"), less than about 0.2 MPa, less than about 0.1 MPa, or less than 0.05 MPa.

Optionally, a continuous or intermittent flush can be provided to oxidant sparger 34 with a liquid (e.g., acetic acid, water, and/or para-xylene) to prevent fouling of the oxidant sparger with solids. When such a liquid flush is employed, an effective amount of the liquid (i.e., not just the minor amount of liquid droplets that might naturally be present in the oxidant stream) can be passed through the oxidant sparger and out of the oxidant openings for at least one period of more than one minute each day. When a liquid is continuously or periodically discharged from oxidant sparger 34, the time-averaged ratio of the mass flow rate of the liquid through the oxidant sparger to the mass flow rate of the molecular oxygen through the oxidant sparger can be in the range of from about 0.05:1 to about 30:1, in the range of from about 0.1:1 to about 2:1, or in the range of from 0.2:1 to 1:1.

In many conventional bubble column reactors containing a multi-phase reaction medium, substantially all of the reaction medium located below the oxidant sparger (or other mechanism for introducing the oxidant stream into the reaction zone) has a very low gas hold-up value. As known in the art, "gas hold-up" is simply the volume fraction of a multi-phase medium that is in the gaseous state. Zones of low gas hold-up in a medium can also be referred to as "unaerated" zones. In many conventional slurry bubble column reactors, a significant portion of the total volume of the reaction medium is located below the oxidant sparger (or other mechanism for introducing the oxidant stream into the reaction zone). Thus, a significant portion of the reaction medium present at the bottom of conventional bubble column reactors is unaerated.

It has been discovered that minimizing the amount of unaerated zones in a reaction medium subjected to oxidization in a bubble column reactor can minimize the generation of certain types of undesirable impurities. Unaerated zones of a reaction medium contain relatively few oxidant bubbles. This low volume of oxidant bubbles reduces the amount of molecular oxygen available for dissolution into the liquid phase of the reaction medium. Thus, the liquid phase in an unaerated zone of the reaction medium has a relatively low concentration of molecular oxygen. These oxygen-starved, unaerated zones of the reaction medium have a tendency to promote undesirable side reactions, rather than the desired oxidation reaction. For example, when para-xylene is partially oxidized to form terephthalic acid, insufficient oxygen availability in the liquid phase of the reaction medium can cause the formation of undesirably high quantities of benzoic acid and coupled aromatic rings, notably including highly undesirable colored molecules known as fluorenones and anthraquinones.

In accordance one or more embodiments, liquid-phase oxidation can be carried out in a bubble column reactor configured and operated in a manner such that the volume fraction of the reaction medium with low gas hold-up values is minimized. This minimization of unaerated zones can be quantified by theoretically partitioning the entire volume of the reaction medium into 2,000 discrete horizontal slices of uniform volume. With the exception of the highest and lowest horizontal slices, each horizontal slice is a discrete volume bounded on its sides by the sidewall of the reactor and bounded on its top and bottom by imaginary horizontal planes. The highest horizontal slice is bounded on its bottom by an imaginary horizontal plane and on its top by the upper surface of the reaction medium. The lowest horizontal slice is bounded on its top by an imaginary horizontal plane and on its bottom by the lower end of the vessel. Once the reaction medium has been theoretically partitioned into 2,000 discrete horizontal slices of equal volume, the time-averaged and volume-averaged gas hold-up of each horizontal slice can be determined. When this method of quantifying the amount of unaerated zones is employed, the number of horizontal slices having a time-averaged and volume-averaged gas hold-up less than 0.1 can be less than 30, less than 15, less than 6, less than 4, or less than 2. Furthermore, the number of horizontal slices having a gas hold-up less than 0.2 can be less than 80, less than 40, less than 20, less than 12, or less than 5. Also, the number of horizontal slices having a gas hold-up less than 0.3 can be less than 120, less than 80, less than 40, less than 20, or less than 15.

Referring still to FIG. 1, it has been discovered that positioning oxidant sparger 34 lower in reaction zone 28 provides several advantages, including reduction of the amount of unaerated zones in reaction medium 36. Given a height "$H_p$" of reaction medium 36, a length "$L_p$" of reaction zone 28, and a maximum diameter "$D_p$" of reaction zone 28, a majority of the oxidant stream can be introduced into reaction zone 28 within about 0.025 $H_p$, 0.022 $L_p$, and/or 0.25 $D_p$ of lower end 52 of reaction zone 28, within about 0.02 $H_p$, 0.018 $L_p$, and/or 0.2 $D_p$ of lower end 52 of reaction zone 28, or within 0.015 $H_p$, 0.013 $L_p$, and/or 0.15 $D_p$ of lower end 52 of reaction zone 28.

In addition to the advantages provided by minimizing unaerated zones (i.e., zones with low gas hold-up) in reaction medium 36, it has been discovered that oxidation can be enhanced by maximizing the gas hold-up of the entire reaction medium 36. Reaction medium 36 can have a time-averaged and volume-averaged gas hold-up of at least about 0.4, in the range of from about 0.6 to about 0.9, or in the range of from 0.65 to 0.85. Several physical and operational attributes of bubble column reactor 20 contribute to the high gas hold-up discussed above. For example, for a given reactor size and flow of oxidant stream, the high $L_p:D_p$ ratio of reaction zone 28 yields a lower diameter which increases the superficial velocity in reaction medium 36 which in turn increases gas hold-up. Additionally, the actual diameter of a bubble column and the $L_p:D_p$ ratio are known to influence the average gas hold-up even for a given constant superficial velocity. In addition, the minimization of unaerated zones, particularly in the bottom of reaction zone 28, contributes to an increased gas hold-up value. Further, the overhead pressure and mechanical configuration of the bubble column reactor can affect operating stability at the high superficial velocities and gas hold-up values disclosed herein.

Referring still to FIG. 1, it has been discovered that improved distribution of the oxidizable compound (e.g., paraxylene) in reaction medium 36 can be provided by introducing the liquid-phase feed stream into reaction zone 28 at multiple vertically-spaced locations. In various embodiments, the liquid-phase feed stream can be introduced into reaction zone 28 via at least 3 feed openings, or at least 4 feed openings. As used herein, the term "feed openings" shall denote openings where the liquid-phase feed stream is discharged into reaction zone 28 for mixing with reaction medium 36. In one or more embodiments, at least 2 of the feed openings can be vertically-spaced from one another by at least about 0.5 $D_p$, at least about 1.5 $D_p$, or at least 3 $D_p$. However, the highest feed opening can be vertically-spaced from the lowest oxidant opening by not more than about 0.75 $H_p$, 0.65 $L_p$, and/or 8 $D_p$; not more than about 0.5 $H_p$, 0.4 $L_p$, and/or 5 $D_p$; or not more than 0.4 $H_p$, 0.35 $L_p$, and/or 4 $D_p$.

Although it is desirable to introduce the liquid-phase feed stream at multiple vertical locations, it has also been discovered that improved distribution of the oxidizable compound in reaction medium 36 is provided if the majority of the liquid-phase feed stream is introduced into the bottom half of reaction medium 36 and/or reaction zone 28. In various embodiments, at least about 75 weight percent or at least 90 weight percent of the liquid-phase feed stream can be introduced into the bottom half of reaction medium 36 and/or reaction zone 28. In addition, at least about 30 weight percent of the liquid-phase feed stream can be introduced into reaction zone 28 within about 1.5 $D_p$ of the lowest vertical location where the oxidant stream is introduced into reaction zone 28. This lowest vertical location where the oxidant stream is introduced into reaction zone 28 is typically at the bottom of oxidant sparger 34; however, a variety of alternative configurations for introducing the oxidant stream into reaction zone 28 are contemplated by various embodiments. In one or more embodiments, at least about 50 weight percent of the liquid-phase feed can be introduced within about 2.5 $D_p$ of the lowest vertical location where the oxidant stream is introduced into reaction zone 28. In other embodiments, at least about 75 weight percent of the liquid-phase feed stream can be introduced within about 5 $D_p$ of the lowest vertical location where the oxidant stream is introduced into reaction zone 28.

Each feed opening defines an open area through which the feed is discharged. In various embodiments, at least about 30 percent of the cumulative open area of all the feed inlets can be located within about 1.5 $D_p$ of the lowest vertical location where the oxidant stream is introduced into reaction zone 28. In other embodiments, at least about 50 percent of the cumulative open area of all the feed inlets can be located within about 2.5 $D_p$ of the lowest vertical location where the oxidant stream is introduced into reaction zone 28. In still other embodiments, at least about 75 percent of the cumulative open area of all the feed inlets can be located within about 5 $D_p$ of the lowest vertical location where the oxidant stream is introduced into reaction zone 28.

Referring still to FIG. 1, in one or more embodiments, feed inlets 32a,b,c,d can simply be a series of vertically-aligned openings along one side of vessel shell 22. These feed openings can have substantially similar diameters of less than about 7 centimeters, in the range of from about 0.25 to about 5 centimeters, or in the range of from 0.4 to 2 centimeters. Bubble column reactor 20 can be equipped with a system for controlling the flow rate of the liquid-phase feed stream out of each feed opening. Such flow control system can include an individual flow control valve 74a,b,c,d for each respective feed inlet 32a,b,c,d. In addition, bubble column reactor 20 can be equipped with a flow control system that allows at least a portion of the liquid-phase feed stream to be introduced into reaction zone 28 at an elevated inlet superficial velocity of at least about 2 meters per second, at least about 5 meters per second, at least about 6 meters per second, or in the range of from 8 to 20 meters per second. As used herein, the term "inlet superficial velocity" denotes the time-averaged volumetric flow rate of the feed stream out of the feed opening divided by the area of the feed opening. In various embodiments, at least about 50 weight percent of the feed stream can be introduced into reaction zone 28 at an elevated inlet superficial velocity. In one or more embodiments, substantially all the feed stream is introduced into reaction zone 28 at an elevated inlet superficial velocity.

Referring now to FIG. 2, there is illustrated a reactor system 100 comprising a primary oxidation reactor 102 and a secondary oxidation reactor 104. Primary oxidation reactor 102 can be configured and operated in substantially the same manner as bubble column reactor 20 described above with reference to FIG. 1.

In one or more embodiments, primary oxidation reactor 102 and secondary oxidation reactor 104 are bubble column reactors. Primary oxidation reactor 102 can include a primary reaction vessel 106 and a primary oxidant sparger 108, while secondary oxidation reactor 104 can include a secondary reaction vessel 110 and a lower oxidant sparger 112. As discussed in greater detail below, secondary oxidation reactor 104 can optionally comprise one or more upper oxidant spargers as well. In one or more embodiments, primary and secondary reaction vessels 106 and 110 can each include a respective upright sidewall having a generally cylindrical configuration. The ratio of the maximum height of the upright sidewall of secondary reaction vessel 110 to the maximum height of the upright sidewall of primary reaction vessel 106 can be in the range of from about 0.1:1 to about 0.9:1, in the range of from about 0.2:1 to about 0.8:1, or in the range of from 0.3:1 to 0.7:1.

Primary reaction vessel 106 defines therein a primary reaction zone 116, while secondary reaction vessel 110 defines therein a secondary reaction zone 118. In various embodiments, the ratio of the maximum horizontal cross sectional area of secondary reaction zone 118 to primary reaction zone 116 can be in the range of from about 0.01:1 to about 0.75:1, in the range of from about 0.02:1 to about 0.5:1, or in the range of from 0.04:1 to 0.3:1. Additionally, the volume ratio of primary reaction zone 116 to secondary reaction zone 118 can be in the range of from about 1:1 to about 100:1, in the range of from about 4:1 to about 50:1, or in the range of from 8:1 to 30:1. Furthermore, primary reaction zone 116 can have a ratio of maximum vertical height to maximum horizontal diameter in the range of from about 3:1 to about 30:1, in the range of from about 6:1 to about 20:1, or in the range of from 9:1 to 15:1.

As shown in FIG. 2, secondary reaction zone 118 can have a maximum vertical length $L_S$ and a maximum horizontal diameter $D_S$. In one or more embodiments, secondary reaction zone 118 can have a ratio of maximum vertical length to maximum horizontal diameter "$L_S:D_S$" in the range of from about 14:1 to about 28:1, in the range of from about 16:1 to about 26:1, in the range of from about 18:1 to about 24:1, in the range of from about 20:1 to about 23:1, or in the range of from 21:1 to 22:1. In various embodiments, $D_S$ of secondary reaction zone 118 can be in the range of from about 0.1 to about 5 meters, in the range of from about 0.3 to about 4 meters, or in the range of from 1 to 3 meters. Furthermore, $L_S$ of secondary reaction zone 118 can be in the range of from about 1 to about 100 meters, in the range of from about 3 to about 50 meters, or in the range of from 10 to 40 meters.

As with bubble column reactor 20 described above with respect to FIG. 1, primary reaction zone 116 has a maximum vertical length $L_p$ and a maximum horizontal diameter $D_p$. In various embodiments, the ratio of the maximum horizontal diameter of secondary reaction zone 118 to the maximum horizontal diameter of primary reaction zone 116 "$D_S:D_p$" can be in the range of from about 0.05:1 to about 0.8:1, in the range of from about 0.1:1 to about 0.6:1, or in the range of from 0.2:1 to 0.5:1. Furthermore, the ratio of the maximum vertical length of secondary reaction zone 118 to the maximum vertical length of primary reaction zone 116 "$L_S:L_p$" can be in the range of from about 0.03:1 to about 1:1, in the range of from about 0.1:1 to about 0.9:1, or in the range of from 0.3:1 to 0.8:1.

In various embodiments, secondary oxidation reactor 104 can be located alongside primary oxidation reactor 102 (i.e., at least a portion of primary and secondary oxidation reactors 102 and 104 share a common elevation). As noted above, primary reaction zone 116 of primary oxidation reactor 102 has a maximum diameter $D_p$. In one or more embodiments, the volumetric centroid of secondary reaction zone 118 can be horizontally spaced from the volumetric centroid of primary reaction zone 416 by at least about 0.5 $D_p$, 0.75 $D_p$, or 1.0 $D_p$ and by less than about 30 $D_p$, 10 $D_p$, or 3 $D_p$.

Any parameters (e.g., height, width, area, volume, relative horizontal placement, and relative vertical placement) specified herein for primary reaction vessel 106 and appurtenances are also construed as applying to primary reaction zone 116 defined by primary reaction vessel 106, and vice versa. Further, any parameters specified herein for secondary reaction vessel 110 and appurtenances are also construed as applying to secondary reaction zone 118 defined by secondary reaction vessel 110, and vice versa.

During normal operation of reactor system 100, reaction medium 120 can first undergo oxidation in primary reaction zone 116 of primary oxidation reactor 102. Reaction medium 120a can then be withdrawn from primary reaction zone 116 and transferred to secondary reaction zone 118 via conduit 105. In secondary reaction zone 118, the liquid and/or solid phases of reaction medium 120b can be subjected to further oxidation. In various embodiments, at least about 50, 75, 95, or 99 weight percent of liquid and/or solid phases withdrawn from primary reaction zone 116 can be processed in secondary reaction zone 116. Overhead gasses can exit an upper gas outlet of secondary oxidation reactor 104 and can be transferred back to primary oxidation reactor 102 via conduit 107. A slurry phase of reaction medium 120b can exit a lower slurry outlet 122 of secondary oxidation reactor 104 and can thereafter be subjected to further downstream processing.

Inlet conduit 105 may attach to primary oxidation reactor 102 at any height. Although not shown in FIG. 2, reaction medium 120 can be mechanically pumped to secondary reaction zone 118 if desired. However, elevation head (gravity) can also be used transfer reaction medium 120 from primary reaction zone 116 through inlet conduit 105 and into secondary reaction zone 118. Accordingly, inlet conduit 105 can be connected on one end to the upper 50, 30, 20, or 10 percent of the total height and/or volume of primary reaction zone 116. In other various embodiments, the slurry outlet (not depicted) through which reaction medium 120a can exit primary oxidation reactor 102 into inlet conduit 105 can be spaced at least 0.1 $L_p$, at least 0.2 $L_p$, or at least 0.3 $L_p$ away from each of the normally top and normally bottom ends of primary reaction zone 116.

In various embodiments, the other end of inlet conduit 105 can be attached in fluid flow communication to a slurry inlet (not depicted) located in the upper 30, 20, 10, or 5 percent of the total height and/or volume of secondary reaction zone 118. In alternate embodiments, the slurry inlet in secondary oxidation reactor 104 can be a mid-level slurry inlet spaced from the bottom of secondary reaction zone 118 by a distance in the range of from about 0.3 $L_S$ to about 0.9 $L_S$, in the range of from about 0.4 $L_S$ to about 0.8 $L_S$, in the range of from about 0.5 $L_S$ to about 0.8 $L_S$, or in the range of from 0.55 $L_S$ to 0.6 $L_S$. Additionally, the slurry inlet in secondary oxidation reactor 104 can be spaced from the bottom of the secondary reaction zone by a distance in the range of from about 9 $D_S$ to about 15 $D_S$, in the range of from about 10 $D_S$ to about 14 $D_S$, or in the range of from 11 $D_S$ to 13 $D_S$. In operation, at least a portion of reaction medium 120a can be introduced into secondary reaction zone 118 via the mid-level slurry inlet. In various embodiments, at least 5 volume percent, at least 10 volume percent, at least 20 volume percent, at least 30 volume percent, at least 50 volume percent, at least 75 volume percent, or 100 volume percent of the total amount of reaction medium 120a introduced into secondary reaction zone 118 can be introduced via the mid-level slurry inlet.

In various embodiments, inlet conduit 105 can be horizontal, substantially horizontal, and/or sloping downward from primary oxidation reactor 102 toward secondary oxidation reactor 104. In one or more embodiments, inlet conduit 105 is horizontal or substantially horizontal, and can be straight or substantially straight. Accordingly, in one or more embodiments, the slurry outlet (not depicted) from the primary oxidation reactor 102 can be at the same or substantially the same vertical elevation as the slurry inlet (not depicted) in secondary oxidation reactor 104.

In various embodiments, outlet conduit 107 may attach to any elevation in secondary oxidation reactor 104. In various embodiments, outlet conduit 107 can be connected to secondary oxidation reactor 104 above the attachment elevation of inlet conduit 105. Furthermore, outlet conduit 107 can attach to the top of secondary oxidation reactor 104. Outlet conduit 107 can attach to primary oxidation reactor 102 above the attachment elevation of inlet conduit 105. In various embodiments, outlet conduit 107 attaches to the upper 30, 20, 10, or 5 percent of the total height and/or volume of primary reaction zone 116. Outlet conduit 107 can be horizontal and/or sloping upward from secondary oxidation reactor 104 toward primary oxidation reactor 102. Although not shown in FIG. 2, outlet conduit 107 may also attach directly to the gas outlet conduit that withdraws gaseous effluent from the top of primary oxidation reactor 102.

The upper extent of secondary reaction zone 116 may be above or below the upper extent of primary reaction zone 118. In various embodiments, the upper extent of primary reaction zone 116 can be within 10 meters above to 50 meters below, 2 meters below to 40 meters below, or 5 meters below to 30 meters below the upper extent of secondary reaction zone 118. The lower extent of secondary reaction zone 118 may be elevated above or below the lower extent of primary reaction zone 116. In various embodiments, the lower extent of primary reaction zone 116 can be elevated within about 40, 20, 5, or 2 meters above or below the lower extent of secondary reaction zone 118.

Lower slurry outlet 122 may exit from any elevation of secondary oxidation reactor 104. In various embodiments, lower slurry outlet 122 can be connected to secondary oxidation reactor 104 below the attachment elevation of inlet conduit 105. In various embodiments, lower slurry outlet 122 attaches to the bottom of secondary oxidation reactor 104 as shown in FIG. 2.

Secondary oxidation reactor 104 can comprise at least one oxidant inlet that permits additional molecular oxygen to be discharged into secondary reaction zone 118. In one or more embodiments, secondary oxidation reactor 104 can comprise at least one normally lower oxidant inlet and at least one normally upper oxidant inlet. In various embodiments, the normally lower oxidant inlet can be spaced from the bottom of secondary reaction zone 118 by less than 0.5 $L_S$, less than 0.4 $L_S$, less than 0.3 $L_S$, or less than 0.2 $L_S$. Additionally, the normally upper oxidant inlet can be spaced from the bottom of secondary reaction zone 118 by at least 0.5 $L_S$, at least 0.6 $L_S$, at least 0.7 $L_S$, at least 0.8 $L_S$, or at least 0.9 $L_S$. In one or more embodiments, secondary oxidation reactor 104 can comprise at least two normally upper oxidant inlets, each spaced from the bottom of the secondary reaction zone 118 by at least 0.5 $L_S$, at least 0.55 $L_S$, at least 0.6 $L_S$, at least 0.7 $L_S$, at least 0.8 $L_S$, or at least 0.9 $L_S$. Additionally, as noted above, secondary oxidation reactor 104 can comprise a slurry inlet that is in fluid-flow communication with inlet conduit 105. In various embodiments, the normally upper oxidant inlet can be spaced less than 0.4 $L_S$, less than 0.3 $L_S$, less than 0.2 $L_S$, or less than 0.1 $L_S$ from the slurry inlet in secondary oxidation reactor 104. In other embodiments, the normally upper oxidant inlet can be spaced above the slurry inlet by less than 0.4 $L_S$, less than 0.3 $L_S$, less than 0.2 $L_S$, or less than 0.1 $L_S$.

During operation, a first portion of the gas-phase oxidant introduced into secondary reaction zone 118 can be introduced via the normally upper oxidant inlet, while a second portion of the gas-phase oxidant can be introduced via the normally lower oxidant inlet. In various embodiments, the first portion of the gas-phase oxidant introduced via the normally upper oxidant inlet can constitute in the range of from about 5 to about 49 percent, in the range of from about 5 to about 35 percent, in the range of from about 10 to about 20 percent, or in the range of from 10 to 15 percent of the total volume of gas-phase oxidant introduced into secondary reaction zone 118. Accordingly, the normally upper oxidant inlet and normally lower oxidant inlet can define between them a total open area for introducing gas-phase oxidant into secondary reaction zone 118. In one or more embodiments, the normally upper oxidant inlet can define in the range of from about 5 to about 49 percent of the total open area, in the range of from about 5 to about 35 percent of the total open area, in the range of from about 10 to about 20 percent of the total open area, or in the range of from 10 to 15 percent of the total open area.

As shown in FIG. 2, the above-mentioned lower oxidant inlet can comprise a lower oxidant sparger 112. Additionally the above-mentioned upper oxidant inlet(s) can comprise one or more upper oxidant spargers 114a,b,c. Referring now to FIG. 3, a cross-section of secondary oxidation reactor 104 is shown along line 3-3, particularly illustrating upper oxidant sparger 114a. As seen in FIG. 3, upper oxidant sparger 114a can comprise a plurality of oxidant discharge openings 124 for introducing gas-phase oxidant into secondary reaction zone 118. Although not shown, each of upper oxidant spargers 114b and 114c can also comprise a plurality of oxidant discharge openings. Similarly, lower oxidant sparger 112 can also comprise a plurality of oxidant discharge openings. In one or more embodiments, at least 50 percent, at least 60 percent, at least 70 percent, at least 80 percent, at least 90 percent, at least 95 percent or at least 99 percent of oxidant discharge openings 124 defined by upper oxidant spargers 114a,b,c can be oriented to discharge a gas-phase oxidant in the normally downward direction. As used herein, the term "downward" shall denote any direction extending below the normally underneath side of upper oxidant spargers 114a,b,c within 15° of vertical. In various embodiments, at least 50 percent, at least 60 percent, at least 70 percent, at least 80 percent, at least 90 percent, at least 95 percent, or at least 99 percent of oxidant discharge openings located in lower oxidant sparger 112 can be oriented to discharge gas-phase oxidant in a normally downward direction and/or at a 45° angle or approximately a 45° angle away from vertically downward.

As noted above, at least a portion of the gas-phase oxidant and the reaction medium 120a introduced into secondary reaction zone 118 can combine to form reaction medium 120b. In one or more embodiments, it may be desirable for reaction medium 120b to have minimal zones of low oxygen concentration. This minimization of low oxygen content zones can be quantified by theoretically partitioning the entire volume of reaction medium 120b into 20 discrete horizontal slices of uniform volume. With the exception of the highest and lowest horizontal slices, each horizontal slice is a discrete volume bounded on its sides by the sidewall of the reactor and bounded on its top and bottom by imaginary horizontal planes. The highest horizontal slice is bounded on its bottom by an imaginary horizontal plane and on its top by the upper surface of the reaction medium or, in the case of a liquid-full column, by the upper end of the vessel. The lowest horizontal slice is bounded on its top by an imaginary horizontal plane and on its bottom by the lower end of the vessel. In various embodiments, when the entire volume of reaction medium 120b is theoretically partitioned into 20 discrete horizontal slices of equal volume, no two adjacent horizontal slices have a combined time-averaged and volume-averaged oxygen content of less than 7, less than 8, less than 9, or less than 10 ppmw. In other embodiments, none of the 20 horizontal slices has a time-averaged and volume-averaged oxygen content of less than 7, less than 8, less than 9, or less than 10 ppmw.

Referring again to FIG. 2, in general, the manner in which the feed, oxidant, and reflux streams are introduced into primary oxidation reactor 102 and the manner in which primary oxidation reactor 102 is operated are substantially the same as described above with reference to bubble column reactor 20 of FIG. 1. However, one difference between primary oxidation reactor 102 (FIG. 2) and bubble column reactor 20 (FIG. 1) is that primary oxidation reactor 102 does not include an outlet that permits the slurry phase of reaction medium 120a to be directly discharged from primary reaction vessel 106 for downstream processing. Rather, primary oxidation reactor 102 requires the slurry phase of reaction medium 120a to first pass through secondary oxidation reactor 104 before being discharged from reactor system 100. As mentioned above, in secondary reaction zone 118 of secondary oxidation reactor 104, reaction medium 120b is subjected to further oxidation to help purify the liquid and/or solid phases of reaction medium 120b.

In a process where para-xylene is fed to reaction zone 116, the liquid phase of reaction medium 120a that exits primary reaction zone 116 and enters secondary reaction zone 118 typically contains at least some para-toluic acid. In various embodiments, a substantial portion of the para-toluic acid entering secondary reaction zone 118 can be oxidized in secondary reaction zone 118. Thus, the time-averaged concentration of para-toluic acid in the liquid phase of reaction medium 120b exiting second reaction zone 118 can be less than the time-averaged concentration of para-toluic acid in the liquid phase of reaction medium 120a/b entering secondary reaction zone 118. In various embodiments, the time-averaged concentration of para-toluic acid in the liquid phase of reaction medium 120b exiting secondary reaction zone 118 can be less than about 50, 10, or 5 percent of the time-averaged concentration of para-toluic acid in the liquid phase of reaction medium 120a/b entering secondary reaction zone 118. The time-averaged concentration of para-toluic acid in the liquid phase of reaction medium 120a/b entering second reaction zone 118 can be at least about 250 ppmw, in the range of from about 500 to about 6,000 ppmw, or in the range of from 1,000 to 4,000 ppmw. By comparison, the time-averaged concentration of para-toluic acid in the liquid phase of reaction medium 120b exiting secondary reaction zone 118 can be less than about 1,000, 250, or 50 ppmw.

As reaction medium 120b is processed in secondary reaction zone 118 of secondary oxidation reactor 104, the gas hold-up of reaction medium 120b can decrease as the slurry phase of reaction medium 120b flows downwardly through secondary reaction zone 118. In various embodiments, the ratio of the time-averaged gas hold-up of reaction medium 120a/b entering secondary reaction zone 118 to reaction medium 120b exiting secondary reaction zone 118 can be at least about 2:1, 10:1, or 25:1. Additionally, the time-averaged gas hold-up of reaction medium 120a/b entering secondary reaction zone 118 can be in the range of from about 0.4 to about 0.9, in the range of from about 0.5 to about 0.8, or in the range of from 0.55 to 0.7. Furthermore, the time-averaged gas hold-up of reaction medium 120b exiting secondary reaction zone 118 can be less than about 0.1, 0.05, or 0.02. In one or more embodiments, the ratio of the time-averaged gas hold-up of reaction medium 120a in primary reaction zone 116 to reaction medium 120b in secondary reaction zone 118 can be greater than about 1:1, in the range of from about 1.25:1 to about 5:1, or in the range of from 1.5:1 to 4:1, where the gas hold-up values are measured at any height of primary and secondary reaction zones 116 and 118, at any corresponding heights of primary and secondary reaction zones 116 and 118, at ¼-height of primary and/or secondary reaction zones 116 and 118, at ½-height of primary and/or secondary reaction zones 116 and 118, at ¾-height of primary and/or secondary reaction zones 116 and 118, and/or are average values over the entire heights of primary and/or secondary reaction zones 116 and 118. In various embodiments, the time-averaged gas hold-up of the portion of reaction medium 120a in primary reaction zone 116 can be in the range of from about 0.4 to about 0.9, in the range of from about 0.5 to about 0.8, or in the range of from 0.55 to 0.70, where the gas hold-up is measured at any height of primary reaction zone 116, at ¼-height of primary reaction zone 116, at ½-height of primary reaction zone 116, at ¾-height of primary reaction zone 116, and/or is an average over the entire height of primary reaction zone 116. Additionally, the time-averaged gas hold-up of the portion of reaction medium 120b in secondary reaction zone 118 can be in the range of from about 0.01 to about 0.6, in the range of from about 0.03 to about 0.3, or in the range of from 0.08 to 0.2, where the gas hold-up is measured at any height of secondary reaction zone 118, at ¼-height of secondary reaction zone 118, at ½-height of secondary reaction zone 118, at ¾-height of secondary reaction zone 118, and/or is an average over the entire height of secondary reaction zone 118.

The temperature of reaction medium 120 can be approximately the same in primary and secondary reaction zones 116 and 118. In various embodiments, such temperature can be in the range of from about 125 to about 200° C., in the range of from about 140 to about 180° C., or in the range of from 150 to 170° C. However, temperature differences can be formed within primary reaction zone 116, such as those described in greater detail below with reference to FIG. 4. In various embodiments, temperature differences of the same magnitudes can also exist within secondary reaction zone 118 and also between primary reaction zone 116 and secondary reaction zone 118. These additional temperature gradients relate to chemical reaction occurring in secondary reaction zone 118, the introduction of additional oxidant to secondary reaction zone 118, and the static pressures extant in secondary reaction zone 118 compared to those in primary reaction zone 116. As disclosed above, in various embodiments, the bubble hold-up can be greater in primary reaction zone 116 than in secondary reaction zone 118. Thus, the static pressure in primary reaction zone 116 can be greater than in secondary reaction zone 118. The magnitude of this pressure difference depends on the magnitude of liquid or slurry density and on the difference in bubble hold-up between the two reaction zones. The magnitude of this pressure difference increases at elevations further below the upper boundary of secondary reaction zone 118.

As seen in FIG. 2, a portion of the total molecular oxygen fed to reactor system 100 is introduced into secondary reaction zone 118 of secondary oxidation reactor 104 via lower oxidant sparger 112 and optionally via one or more upper oxidant spargers 114a,b,c. In various embodiments, the majority of the total molecular oxygen fed to reactor system 100 can be introduced into primary reaction zone 116, with the balance being introduced into secondary reaction zone 118. In one or more embodiments, at least about 70, 90, 95, or 98 mole percent of the total molecular oxygen fed to reactor system 100 can be introduced into primary reaction zone 116. Furthermore, the molar ratio of the amount of molecular oxygen introduced into primary reaction zone 116 to the amount of molecular oxygen introduced into secondary reaction zone 118 can be at least about 2:1, in the range of from about 4:1 to about 200:1, or in the range of from 10:1 to 100:1. Although it is possible for some of the solvent and/or oxidizable compound (e.g., para-xylene) to be fed directly to secondary reaction zone 118, in various embodiments, less than about 10, 5, or 1 weight percent of the total amount of solvent and/or oxidizable compound fed to reactor system 100 is fed directly to secondary reaction zone 118.

The volume, residence time, and space time rate of reaction medium 120a in primary reaction zone 116 of primary reaction vessel 106 can be, in various embodiments, substantially greater than the volume, residence time, and space time rate of reaction medium 120b in secondary reaction zone 118 of secondary reaction vessel 110. Therefore, the majority of the oxidizable compound (e.g., para-xylene) fed to reactor system 100 can be oxidized in primary reaction zone 116. In various embodiments, at least about 80, 90, or 95 weight percent of all the oxidizable compound that is oxidized in reactor system 100 can be oxidized in primary reaction zone 116.

In one or more embodiments, the time-averaged superficial gas velocity of reaction medium 120a in primary reaction zone 116 can be at least about 0.2, 0.4, 0.8, or 1 meter per second, where the superficial gas velocity is measured at any height of primary reaction zone 116, at ¼-height of primary reaction zone 116, at ½-height of primary reaction zone 116, at ¾-height of primary reaction zone 116, and/or is an average over the entire height of primary reaction zone 116. Although reaction medium 120b in secondary reaction zone 118 can have the same superficial gas velocity as reaction medium 120a in primary reaction zone 116, in various embodiments the time-averaged superficial gas velocity of reaction medium 120b in secondary reaction zone 118 can be less than the time-averaged superficial gas velocity of reaction medium 120a in primary reaction zone 116. This reduced superficial gas velocity in secondary reaction zone 118 is made possible by, for example, the reduced demand for molecular oxygen in secondary reaction zone 118 compared to primary reaction zone 116. The ratio of the time-averaged superficial gas velocity of reaction medium 120a in primary reaction zone 116 to reaction medium 120b in secondary reaction zone 118 can be at least about 1.25:1, 2:1, or 5:1, where the superficial gas velocities are measured at any height of primary and secondary reaction zones 116 and 118, at any corresponding heights of primary and secondary reaction zones 116 and 118, at ¼-height of primary and/or secondary reaction zones 116 and 118, at ½-height of primary and/or secondary reaction zones 116 and 118, at ¾-height of primary and/or secondary reaction zones 116 and 118, and/or are average values over the entire heights of primary and/or secondary reaction zones 116 and 118. In various embodiments, the time-averaged and volume-averaged superficial gas velocity of reaction medium 120b in secondary reaction zone 118 can be less than about 0.2, 0.1, or 0.06 meters per second, where the superficial gas velocity is measured at any height of secondary reaction zone 118, at ¼-height of secondary reaction zone 118, at ½-height of secondary reaction zone 118, at ¾-height of secondary reaction zone 118, and/or is an average over the entire height of secondary reaction zone 118. With these lower superficial gas velocities, downward flow of the slurry phase of reaction medium 120b in secondary reaction zone 118 can be made to move directionally toward plug flow. For example, during oxidation of para-xylene to form TPA, the relative vertical gradient of liquid phase concentration of para-toluic acid can be much greater in secondary reaction zone 118 than in primary reaction zone 116. This is notwithstanding that secondary reaction zone 118 is a bubble column having axial mixing of liquid and of slurry compositions. The time-averaged superficial velocity of the slurry phase (solid+liquid) and the liquid phase of reaction medium 120b in secondary reaction zone 118 can be less than about 0.2, 0.1, or 0.06 meters per second, where the superficial velocity is measured at any height of secondary reaction zone 118, at ¼-height of secondary reaction zone 118, at ½-height of secondary reaction zone 118, at ¾-height of secondary reaction zone 118, and/or is an average over the entire height of secondary reaction zone 118.

In various embodiments, the liquid phase of reaction medium 120b located in secondary reaction zone 118 can have a mass-averaged residence time in secondary reaction zone 118 of at least about 1 minute, in the range of from about 2 to about 60 minutes, or in the range of from 5 to 30 minutes.

As mentioned above, certain physical and operational features of the bubble column reactors, described above with reference to FIG. 1, provide for vertical gradients in the pressure, temperature, and reactant (i.e., oxygen and oxidizable compound) concentrations of the processed reaction medium. As discussed above, these vertical gradients can provide for a more effective and economical oxidation process as compared to conventional oxidation processes, which favor a well-mixed reaction medium of relatively uniform pressure, temperature, and reactant concentration throughout. The vertical gradients for oxygen, oxidizable compound (e.g., para-xylene), and temperature made possible by employing an oxidation system in accordance with an embodiment of the present invention will now be discussed in greater detail.

Figure 4:
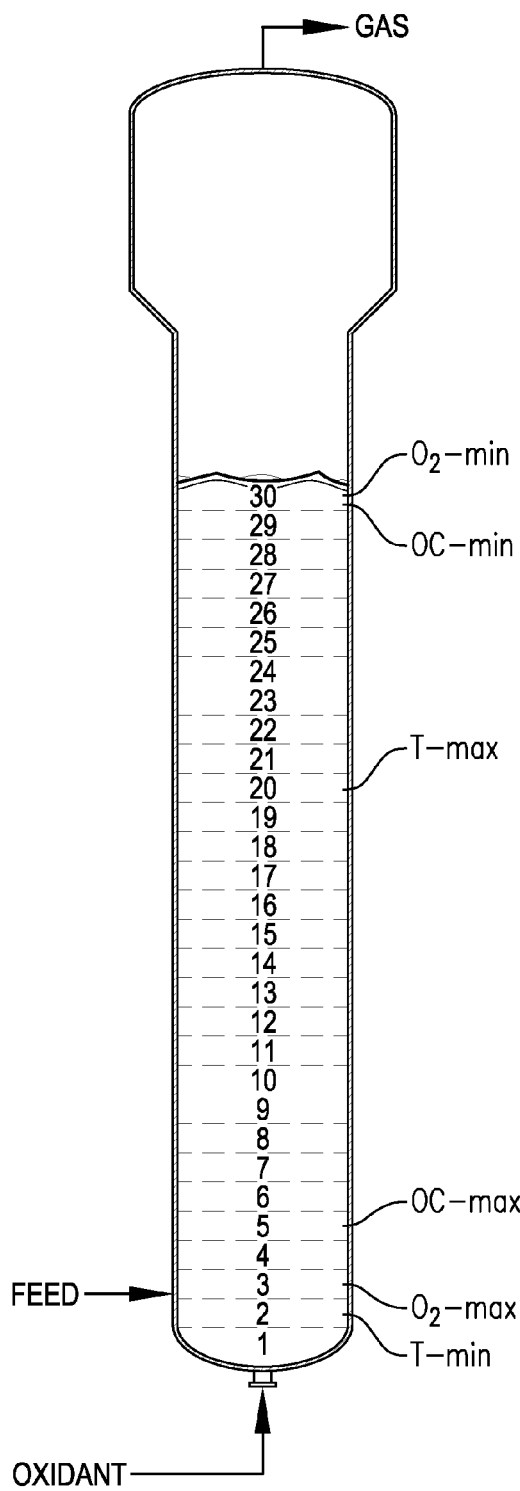
FIG. 4 is a side view of a bubble column reactor containing a multi-phase reaction medium, particularly illustrating the reaction medium being theoretically partitioned into 30 horizontal slices of equal volume in order to quantify certain gradients in the reaction medium.

Referring now to FIG. 4, in order to quantify the reactant concentration gradients existing in the reaction medium during oxidation in the bubble column reactor, the entire volume of the reaction medium can be theoretically partitioned into 30 discrete horizontal slices of equal volume. FIG. 4 illustrates the concept of dividing the reaction medium into 30 discrete horizontal slices of equal volume. With the exception of the highest and lowest horizontal slices, each horizontal slice is a discrete volume bounded on its top and bottom by imaginary horizontal planes and bounded on its sides by the wall of the reactor. The highest horizontal slice is bounded on its bottom by an imaginary horizontal plane and on its top by the upper surface of the reaction medium. The lowest horizontal slice is bounded on its top by an imaginary horizontal plane and on its bottom by the bottom of the vessel shell. Once the reaction medium has been theoretically partitioned into 30 discrete horizontal slices of equal volume, the time-averaged and volume-averaged concentration of each horizontal slice can then be determined. The individual horizontal slice having the maximum concentration of all 30 horizontal slices can be identified as the "C-max horizontal slice." The individual horizontal slice located above the C-max horizontal slice and having the minimum concentration of all horizontal slices located above the C-max horizontal slice can be identified as the "C-min horizontal slice." The vertical concentration gradient can then be calculated as the ratio of the concentration in the C-max horizontal slice to the concentration in the C-min horizontal slice.

With respect to quantifying the oxygen concentration gradient, when the reaction medium is theoretically partitioned into 30 discrete horizontal slices of equal volume, an $O_2$-max horizontal slice is identified as having the maximum oxygen concentration of all the 30 horizontal slices and an $O_2$-min horizontal slice is identified as having the minimum oxygen concentration of the horizontal slices located above the $O_2$-max horizontal slice. The oxygen concentrations of the horizontal slices are measured in the gas phase of the reaction medium on a time-averaged and volume-averaged molar wet basis. In various embodiments, the ratio of the oxygen concentration of the $O_2$-max horizontal slice to the oxygen concentration of the $O_2$-min horizontal slice can be in the range of from about 2:1 to about 25:1, in the range of from about 3:1 to about 15:1, or in the range of from 4:1 to 10:1.

Typically, the $O_2$-max horizontal slice will be located near the bottom of the reaction medium, while the $O_2$-min horizontal slice will be located near the top of the reaction medium. In one or more embodiments, the $O_2$-min horizontal slice can be one of the 5 upper-most horizontal slices of the 30 discrete horizontal slices. Additionally, the $O_2$-min horizontal slice can be the upper-most one of the 30 discrete horizontal slices, as illustrated in FIG. 4. In various embodiments, the $O_2$-max horizontal slice can be one of the 10 lower-most horizontal slices of the 30 discrete horizontal slices. Additionally, the $O_2$-max horizontal slice can be one of the 5 lower-most horizontal slices of the 30 discrete horizontal slices. For example, FIG. 4 illustrates the $O_2$-max horizontal slice as the third horizontal slice from the bottom of the reactor. In one or more embodiments, the vertical spacing between the $O_2$-min and $O_2$-max horizontal slices can be at least about 2 $W_p$, at least about 4 $W_p$, or at least 6 $W_p$. Additionally, the vertical spacing between the $O_2$-min and $O_2$-max horizontal slices can be at least about 0.2 $H_p$, at least about 0.4 $H_p$, or at least 0.6 $H_p$.

The time-averaged and volume-averaged oxygen concentration, on a wet basis, of the $O_2$-min horizontal slice can be in the range of from about 0.1 to about 3 mole percent, in the range of from about 0.3 to about 2 mole percent, or in the range of from 0.5 to 1.5 mole percent. The time-averaged and volume-averaged oxygen concentration of the $O_2$-max horizontal slice can be in the range of from about 4 to about 20 mole percent, in the range of from about 5 to about 15 mole percent, or in the range of from 6 to 12 mole percent. The time-averaged concentration of oxygen, on a dry basis, in the gaseous effluent discharged from the reactor via the gas outlet can be in the range of from about 0.5 to about 9 mole percent, in the range of from about 1 to about 7 mole percent, or in the range of from 1.5 to 5 mole percent.

Because the oxygen concentration decays so markedly toward the top of the reaction medium, the demand for oxygen can be reduced in the top of the reaction medium. This reduced demand for oxygen near the top of the reaction medium can be accomplished by creating a vertical gradient in the concentration of the oxidizable compound (e.g., para-xylene), where the minimum concentration of oxidizable compound is located near the top of the reaction medium.

With respect to quantifying the oxidizable compound (e.g., para-xylene) concentration gradient, when the reaction medium is theoretically partitioned into 30 discrete horizontal slices of equal volume, an OC-max horizontal slice is identified as having the maximum oxidizable compound concentration of all the 30 horizontal slices and an OC-min horizontal slice is identified as having the minimum oxidizable compound concentration of the horizontal slices located above the OC-max horizontal slice. The oxidizable compound concentrations of the horizontal slices are measured in the liquid phase on a time-averaged and volume-averaged mass fraction basis. In various embodiments, the ratio of the oxidizable compound concentration of the OC-max horizontal slice to the oxidizable compound concentration of the OC-min horizontal slice can be greater than about 5:1, greater than about 10:1, greater than about 20:1, or in the range of from 40:1 to 1000:1.

Typically, the OC-max horizontal slice will be located near the bottom of the reaction medium, while the OC-min horizontal slice will be located near the top of the reaction medium. In one or more embodiments, the OC-min horizontal slice can be one of the 5 upper-most horizontal slices of the 30 discrete horizontal slices. Additionally, the OC-min horizontal slice can be the upper-most one of the 30 discrete horizontal slices, as illustrated in FIG. 4. In various embodiments, the OC-max horizontal slice can be one of the 10 lower-most horizontal slices of the 30 discrete horizontal slices. Additionally, the OC-max horizontal slice can be one of the 5 lower-most horizontal slices of the 30 discrete horizontal slices. For example, FIG. 4 illustrates the OC-max horizontal slice as the fifth horizontal slice from the bottom of the reactor. In various embodiments, the vertical spacing between the OC-min and OC-max horizontal slices can be at least about 2 $W_p$ (where "$W_p$" is the maximum width of the reaction medium), at least about 4 $W_p$, or at least 6 $W_p$. Given a height "$H_p$" of the reaction medium, the vertical spacing between the OC-min and OC-max horizontal slices can be at least about 0.2 $H_p$, at least about 0.4 $H_p$, or at least 0.6 $H_p$.

The time-averaged and volume-averaged oxidizable compound (e.g., para-xylene) concentration in the liquid phase of the OC-min horizontal slice can be less than about 5,000 ppmw, less than about 2,000 ppmw, less than about 400 ppmw, or in the range of from 1 ppmw to 100 ppmw. The time-averaged and volume-averaged oxidizable compound concentration in the liquid phase of the OC-max horizontal slice can be in the range of from about 100 ppmw to about 10,000 ppmw, in the range of from about 200 ppmw to about 5,000 ppmw, or in the range of from 500 ppmw to 3,000 ppmw.

Although the bubble column reactor can provide vertical gradients in the concentration of the oxidizable compound, the volume percent of the reaction medium having an oxidizable compound concentration in the liquid phase above 1,000 ppmw can also be minimized. In various embodiments, the time-averaged volume percent of the reaction medium having an oxidizable compound concentration in the liquid phase above 1,000 ppmw can be less than about 9 percent, less than about 6 percent, or less than 3 percent. Additionally, the time-averaged volume percent of the reaction medium having an oxidizable compound concentration in the liquid phase above 2,500 ppmw can be less than about 1.5 percent, less than about 1 percent, or less than 0.5 percent. Furthermore, the time-averaged volume percent of the reaction medium having an oxidizable compound concentration in the liquid phase above 10,000 ppmw can be less than about 0.3 percent, less than about 0.1 percent, or less than 0.03 percent. Also, the time-averaged volume percent of the reaction medium having an oxidizable compound concentration in the liquid phase above 25,000 ppmw can be less than about 0.03 percent, less than about 0.015 percent, or less than 0.007 percent. The inventors note that the volume of the reaction medium having the elevated levels of oxidizable compound need not lie in a single contiguous volume. At many times, the chaotic flow patterns in a bubble column reaction vessel produce simultaneously two or more continuous but segregated portions of the reaction medium having the elevated levels of oxidizable compound. At each time used in the time averaging, all such continuous but segregated volumes larger than 0.0001 volume percent of the total reaction medium are added together to determine the total volume having the elevated levels of oxidizable compound concentration in the liquid phase.

In addition to the concentration gradients of oxygen and oxidizable compound, discussed above, a temperature gradient can exist in the reaction medium. Referring again to FIG. 4, this temperature gradient can be quantified in a manner similar to the concentration gradients by theoretically partitioning the reaction medium into 30 discrete horizontal slices of equal volume and measuring the time-averaged and volume-averaged temperature of each slice. The horizontal slice with the lowest temperature out of the lowest 15 horizontal slices can then be identified as the T-min horizontal slice, and the horizontal slice located above the T-min horizontal slice and having the maximum temperature of all the slices above the T-min horizontal slice can then be identified as the T-max horizontal slice. In various embodiments, the temperature of the T-max horizontal slice can be at least about 1° C. higher than the temperature of the T-min horizontal slice, in the range of from about 1.25 to about 12° C. higher than the temperature of the T-min horizontal slice, or in the range of from 2 to 8° C. higher than the temperature of the T-min horizontal slice. The temperature of the T-max horizontal slice can be in the range of from about 125 to about 200° C., in the range of from about 140 to about 180° C., or in the range of from 150 to 170° C.

Typically, the T-max horizontal slice will be located near the center of the reaction medium, while the T-min horizontal slice will be located near the bottom of the reaction medium. In various embodiments, the T-min horizontal slice can be one of the 10 lower-most horizontal slices of the 15 lowest horizontal slices, or one of the 5 lower-most horizontal slices of the 15 lowest horizontal slices. For example, FIG. 4 illustrates the T-min horizontal slice as the second horizontal slice from the bottom of the reactor. In various embodiments, the T-max horizontal slice can be one of the 20 middle horizontal slices of the 30 discrete horizontal slices, or one of the 14 middle horizontal slices of the 30 discrete horizontal slices. For example, FIG. 4 illustrates the T-max horizontal slice as the twentieth horizontal slice from the bottom of the reactor (i.e., one of the middle 10 horizontal slices). The vertical spacing between the T-min and T-max horizontal slices can be at least about 2 $W_p$, at least about 4 $W_p$, or at least 6 $W_p$. The vertical spacing between the T-min and T-max horizontal slices can be at least about 0.2 $H_p$, at least about 0.4 $H_p$, or at least 0.6 $H_p$.

As discussed above, when a vertical temperature gradient exists in the reaction medium, it can be advantageous to withdraw the reaction medium at an elevated location where the temperature of reaction medium is highest, especially when the withdrawn product is subjected to further downstream processing at higher temperatures. Thus, when reaction medium 120 is withdrawn from the reaction zone via one or more elevated outlets, as illustrated in FIG. 2, the elevated outlet(s) can be located near the T-max horizontal slice. In various embodiments, the elevated outlet can be located within 10 horizontal slices of the T-max horizontal slice, within 5 horizontal slices of the T-max horizontal slice, or within 2 horizontal slices of the T-max horizontal slice.

It is now noted that many of the inventive features described herein can be employed in multiple oxidation reactor systems—not just systems employing a single oxidation reactor. In addition, certain inventive features described herein can be employed in mechanically-agitated and/or flow-agitated oxidation reactors—not just bubble-agitated reactors (i.e., bubble column reactors). For example, the inventors have discovered certain advantages associated with staging/varying oxygen concentration and/or oxygen consumption rate throughout the reaction medium. The advantages realized by the staging of oxygen concentration/consumption in the reaction medium can be realized whether the total volume of the reaction medium is contained in a single vessel or in multiple vessels. Further, the advantages realized by the staging of oxygen concentration/consumption in the reaction medium can be realized whether the reaction vessel (s) is mechanically-agitated, flow-agitated, and/or bubble-agitated.

Figure 5:
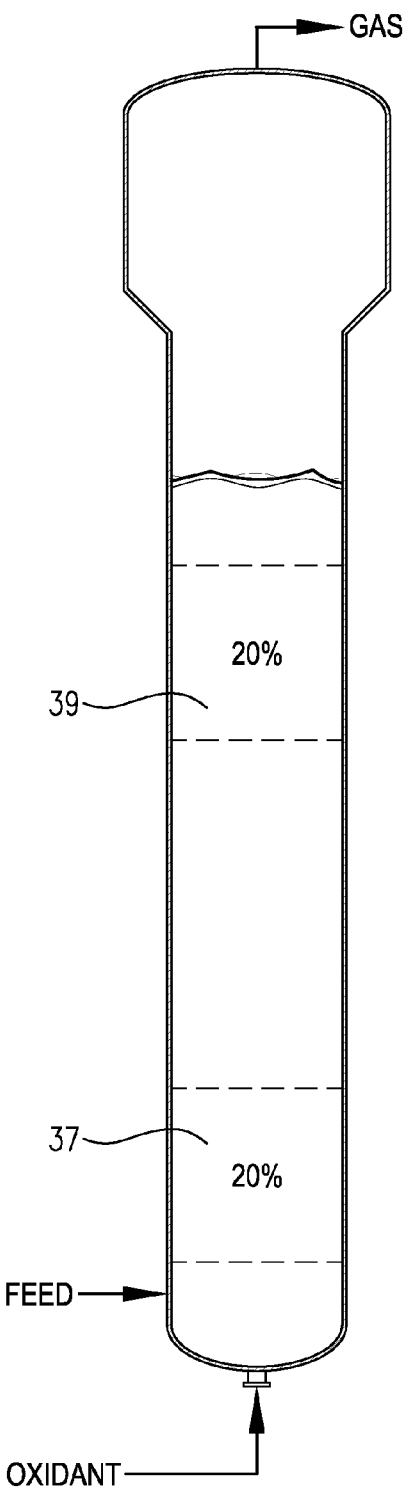
FIG. 5 is a side view of a bubble column reactor containing a multi-phase reaction medium, particularly illustrating first and second discrete 20-percent continuous volumes of the reaction medium that have substantially different oxygen concentrations and/or oxygen consumption rates.

One way of quantifying the degree of staging of oxygen concentration and/or consumption rate in a reaction medium is to compare two or more distinct 20-percent continuous volumes of the reaction medium. These 20-percent continuous volumes need not be defined by any particular shape. However, each 20-percent continuous volume must be formed of a contiguous volume of the reaction medium (i.e., each volume is "continuous"), and the 20-percent continuous volumes must not overlap one another (i.e., the volumes are "distinct"). These distinct 20-percent continuous volumes can be located in the same reactor or in multiple reactors. Referring now to FIG. 5, the bubble column reactor is illustrated as containing a reaction medium that includes a first distinct 20-percent continuous volume 37 and a second distinct 20-percent continuous volume 39.

The staging of oxygen availability in the reaction medium can be quantified by referring to the 20-percent continuous volume of reaction medium having the most abundant mole fraction of oxygen in the gas phase and by referring to the 20-percent continuous volume of reaction medium having the most depleted mole fraction of oxygen in the gas phase. In the gas phase of the distinct 20-percent continuous volume of the reaction medium containing the highest concentration of oxygen, the time-averaged and volume-averaged oxygen concentration, on a wet basis, can be in the range of from about 3 to about 18 mole percent, in the range of from about 3.5 to about 14 mole percent, or in the range of from 4 to 10 mole percent. In the gas phase of the distinct 20-percent continuous volume of the reaction medium containing the lowest concentration of oxygen, the time-averaged and volume-averaged oxygen concentration, on a wet basis, can be in the range of from about 0.3 to about 5 mole percent, in the range of from about 0.6 to about 4 mole percent, or in the range of from 0.9 to 3 mole percent. Furthermore, the ratio of the time-averaged and volume-averaged oxygen concentration, on a wet basis, in the most abundant 20-percent continuous volume of reaction medium compared to the most depleted 20-percent continuous volume of reaction medium can be in the range of from about 1.5:1 to about 20:1, in the range of from about 2:1 to about 12:1, or in the range of from 3:1 to 9:1.

The staging of oxygen consumption rate in the reaction medium can be quantified in terms of an oxygen-STR, initially described above. Oxygen-STR was previously describe in a global sense (i.e., from the perspective of the average oxygen-STR of the entire reaction medium); however, oxygen-STR may also be considered in a local sense (i.e., a portion of the reaction medium) in order to quantify staging of the oxygen consumption rate throughout the reaction medium.

The inventors have discovered that it can be useful to cause the oxygen-STR to vary throughout the reaction medium in general harmony with the desirable gradients disclosed herein relating to pressure in the reaction medium and to the mole fraction of molecular oxygen in the gas phase of the reaction medium. Thus, in various embodiments, the ratio of the oxygen-STR of a first distinct 20-percent continuous volume of the reaction medium compared to the oxygen-STR of a second distinct 20-percent continuous volume of the reaction medium can be in the range of from about 1.5:1 to about 20:1, in the range of from about 2:1 to about 12:1, or in the range of from 3:1 to 9:1. In one embodiment, the "first distinct 20-percent continuous volume" can be located closer than the "second distinct 20-percent continuous volume" to the location where molecular oxygen is initially introduced into the reaction medium. These large gradients in oxygen-STR may be desirable whether the partial oxidation reaction medium is contained in a bubble column oxidation reactor or in any other type of reaction vessel in which gradients are created in pressure and/or mole fraction of molecular oxygen in the gas phase of the reaction medium (e.g., in a mechanically agitated vessel having multiple, vertically disposed stirring zones achieved by using multiple impellers having strong radial flow, possibly augmented by generally horizontal baffle assemblies, with oxidant flow rising generally upwards from a feed near the lower portion of the reaction vessel, notwithstanding that considerable back-mixing of oxidant flow may occur within each vertically disposed stiffing zone and that some back-mixing of oxidant flow may occur between adjacent vertically disposed stirring zones). That is, when a gradient exists in the pressure and/or mole fraction of molecular oxygen in the gas phase of the reaction medium, the inventors have discovered that it may be desirable to create a similar gradient in the chemical demand for dissolved oxygen.

One way of causing the local oxygen-STR to vary is by controlling the locations of feeding the oxidizable compound and by controlling the mixing of the liquid phase of the reaction medium to control gradients in concentration of oxidizable compound according to other disclosures herein. Other useful means of causing the local oxygen-STR to vary include causing variation in reaction activity by causing local temperature variation and by changing the local mixture of catalyst and solvent components (e.g., by introducing an additional gas to cause evaporative cooling in a particular portion of the reaction medium and/or by adding a solvent stream containing a higher amount of water to decrease activity in a particular portion of the reaction medium).

Figure 6:
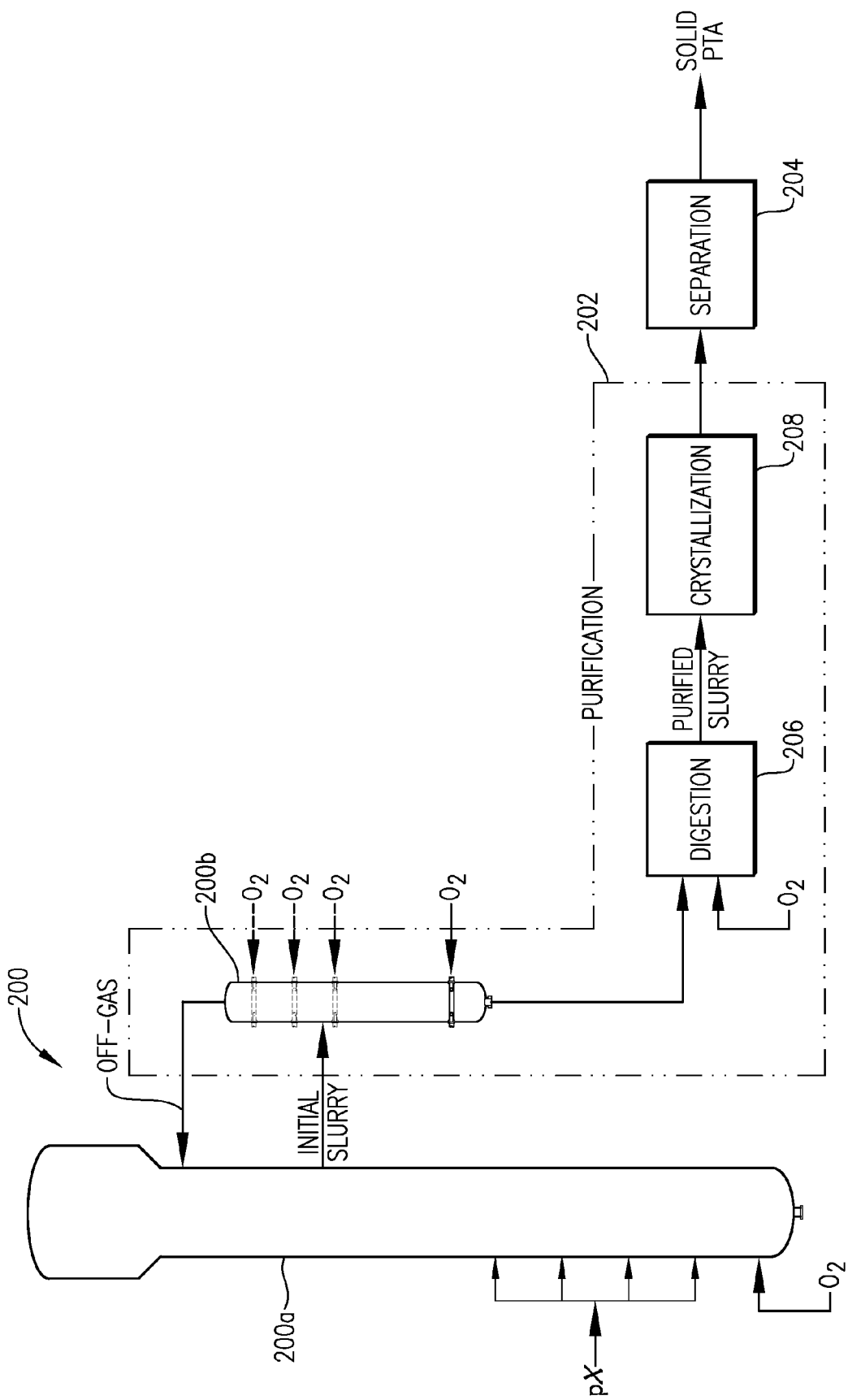
FIG. 6 is a simplified process flow diagram of a process for making PTA in accordance with an embodiment of the present invention.

Referring now to FIG. 6, a process is illustrated for producing purified terephthalic acid ("PTA") employing an oxidation reactor system 200 comprising a primary oxidation reactor 200a and a secondary oxidation reactor 200b. In the configuration illustrated in FIG. 6, an initial slurry can be produced from primary oxidation reactor 200a and can thereafter be subjected to purification in a purification system 202, of which secondary oxidation reactor 200b is a part. The initial slurry withdrawn from primary oxidation reactor 200a can comprise solid crude terephthalic acid ("CTA") particles and a liquid mother liquor. Typically, the initial slurry can contain in the range of from about 10 to about 50 weight percent solid CTA particles, with the balance being liquid mother liquor. The solid CTA particles present in the initial slurry withdrawn from primary oxidation reactor 200a can contain at least about 400 ppmw of 4-carboxybenzaldehyde ("4-CBA"), at least about 800 ppmw of 4-CBA, or in the range of from 1,000 to 15,000 ppmw of 4-CBA.

Purification system 202 receives the initial slurry withdrawn from primary oxidation reactor 200a and reduces the concentration of 4-CBA and other impurities present in the CTA. A purer/purified slurry can be produced from purification system 202 and can be subjected to separation and drying in a separation system 204 to thereby produce purer solid terephthalic acid particles comprising less than about 400 ppmw of 4-CBA, less than about 250 ppmw of 4-CBA, or in the range of from 10 to 200 ppmw of 4-CBA.

Purification system 202 includes secondary oxidation reactor 200b, a digester 206, and a single crystallizer 208. In secondary oxidation reactor 200b, the initial slurry is subjected to oxidation at conditions such as described above with reference to secondary oxidation reactor 104 of FIG. 2. The slurry exiting secondary oxidation reactor 200b is introduced into digester 206. In digester 206, a further oxidation reaction can be performed at slightly higher temperatures than were used in primary oxidation reactor 200a.

The high surface area, small particle size, and low density of the CTA particles produced in primary oxidation reactor 200a can cause certain impurities trapped in the CTA particles to become available for oxidation in digester 206 without requiring complete dissolution of the CTA particles in digester 206. Thus, the temperature in digester 206 can be lower than many similar prior art processes. The further oxidation carried out in digester 206 can reduce the concentration of 4-CBA in the CTA by at least 200 ppmw, at least about 400 ppmw, or in the range of from 600 to 6,000 ppmw. The digestion temperature in digester 206 can be at least about 10° C. higher than the primary oxidation temperature in reactor 200a, about 20 to about 80° C. higher than the primary oxidation temperature in reactor 200a, or 30 to 50° C. higher than the primary oxidation temperature in reactor 200a. The digestion temperature can be in the range of from about 160 to about 240° C., in the range of from about 180 to about 220° C., or in the range of from 190 to 210° C. In various embodiments, the purified product from digester 206 needs only a single crystallization step in crystallizer 208 prior to separation in separation system 204. Suitable secondary oxidation/digestion techniques are discussed in further detail in U.S. Pat. No. 7,132,566, the entire disclosure of which is expressly incorporated herein by reference.

Terephthalic acid (e.g., PTA) produced by the system illustrated in FIG. 6 can be formed of PTA particles having a mean particle size of at least about 40 micrometers (μm), in the range of from about 50 to about 2,000 μm, or in the range of from 60 to 200 μm. The PTA particles can have an average BET surface area less than about 0.25 $m^2/g$, in the range of from about 0.005 to about 0.2 $m^2/g$, or in the range of from 0.01 to 0.18 $m^2/g$. PTA produced by the system illustrated in FIG. 6 is suitable for use as a feedstock in the making of PET. Typically, PET is made via esterification of terephthalic acid with ethylene glycol, followed by polycondensation. In various embodiments, terephthalic acid produced by an embodiment of the present invention can be employed as a feed to the pipe reactor PET process described in U.S. Pat. No. 6,861,494, the entire disclosure of which is incorporated herein by reference.

CTA particles with the morphology disclosed herein may be particularly useful in the above-described oxidative digestion process for reduction of 4-CBA content. In addition, these CTA particles may provide advantages in a wide range of other post-processes involving dissolution and/or chemical reaction of the particles. These additional post-processes include, but are not limited too, reaction with at least one hydroxyl-containing compound to form ester compounds, especially the reaction of CTA with methanol to form dimethyl terephthalate and impurity esters; reaction with at least one diol to form ester monomer and/or polymer compounds, especially the reaction of CTA with ethylene glycol to form polyethylene terephthalate (PET); and full or partial dissolution in solvents, including, but not limited too, water, acetic acid, and N-methyl-2-pyrrolidone, which may include further processing, including, but not limited too, reprecipitation of a more pure terephthalic acid and/or selective chemical reduction of carbonyl groups other than carboxylic acid groups. Notably included is the substantial dissolution of CTA in a solvent comprising water coupled with partial hydrogenation that reduces the amount of aldehydes, especially 4-CBA, fluorenones, phenones, and/or anthraquinones.

DEFINITIONS

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively.

Claims Not Limited to Disclosed Embodiments

The forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

We claim:

1. A system for producing a polycarboxylic acid by contacting a slurry with a gas-phase oxidant, said system comprising:
a primary oxidation reactor comprising a first slurry outlet; and
a secondary oxidation reactor comprising:
a secondary reaction zone having a maximum length $L_S$ and a maximum diameter $D_S$,
a slurry inlet spaced from the bottom of said secondary reaction zone by a distance in the range of from about 0.3 $L_S$ to about 0.9 $L_S$;
a normally upper oxidant inlet spaced less than 0.4 $L_S$ from said slurry inlet;
a normally lower oxidant inlet spaced from the bottom of said secondary reaction zone by less than 0.3 $L_S$; and
a second slurry outlet;
wherein said slurry inlet is in downstream fluid-flow communication with said first slurry outlet.

2. The system of claim 1, wherein said primary oxidation reactor comprises a reaction zone with an oxidant sparger, wherein said oxidant sparger consists of a primary oxidant sparger located in a lower portion of the reaction zone.

3. The system of claim 1, wherein said normally upper oxidant inlet is spaced from the bottom of said secondary reaction zone by at least 0.5 $L_S$.

4. The system of claim 2, wherein said primary oxidation reactor comprises a reaction zone having a maximum length $L_p$ and a maximum diameter $D_p$ and a ratio $L_p/D_p$ is from 6/1 to 30/1.

5. The system of claim 1, wherein said slurry inlet is spaced from the bottom of said secondary reaction zone by a distance in the range of from about 0.5 $L_S$ to about 0.8 $L_S$.

6. The system of claim 1, wherein said slurry inlet is spaced from the bottom of said secondary reaction zone by a distance in the range of from about 9 $D_S$ to about 15 $D_S$.

7. The system of claim 1, wherein said secondary reaction zone has an $L_S:D_S$ ratio in the range of from about 14:1 to about 28:1.

8. The system of claim 1, wherein said first slurry outlet and said slurry inlet have substantially the same vertical elevation, wherein said first slurry outlet and said slurry inlet are coupled in fluid-flow communication via a substantially straight and substantially horizontal conduit.

9. The system of claim 1, wherein said primary oxidation reactor is a bubble column reactor, wherein said secondary oxidation reactor is a bubble column reactor.

10. The system of claim 4, wherein said first slurry outlet is spaced at least 0.1 $L_p$ away from each of the normally top and normally bottom ends of said primary reaction zone.

11. The system of claim 10, wherein the volume ratio of said primary reaction zone to said secondary reaction zone is in the range of from about 4:1 to about 50:1.

12. A method for making a polycarboxylic acid composition, said method comprising:
(a) subjecting a first multi-phase reaction medium comprising an oxidizable compound to oxidation in a primary reaction zone defined in a primary oxidation reactor to thereby produce a first slurry; and
(b) contacting at least a portion of said first slurry with a gas-phase oxidant in a secondary reaction zone defined in a secondary oxidation reactor to thereby produce a second slurry,
wherein said secondary reaction zone has a maximum length $L_S$ and a maximum diameter $D_S$,
a normally upper oxidant inlet spaced less than 0.4 $L_S$ from said slurry inlet;
a normally lower oxidant inlet spaced from the bottom of said secondary reaction zone by less than 0.3 $L_S$;
wherein at least a portion of said first slurry is introduced into said secondary reaction zone at a slurry inlet region spaced from the bottom of said secondary reaction zone by a distance in the range of from about 0.3 $L_S$ to about 0.94 $L_S$.

13. The method of claim 12, wherein said primary oxidation reactor comprises a reaction zone with an oxidant sparger, wherein said oxidant sparger consists of a primary oxidant sparger located in a lower portion of the reaction zone.

14. The method of claim 13, wherein said first oxidant inlet region is spaced from the bottom of said secondary reaction zone by at least 0.5 $L_S$.

15. The method of claim 13, wherein said primary oxidation reactor comprises a reaction zone having a maximum length $L_p$ and a maximum diameter $D_p$ and a ratio $L_p/D_p$ is from 6/1 to 30/1.

16. The method of claim 12, wherein at least 75 weight percent of said first slurry is introduced into said secondary reaction zone at said slurry inlet region, wherein said slurry inlet region is spaced from the bottom of said secondary reaction zone by a distance in the range of from about 0.5 $L_S$ to about 0.8 $L_S$.

17. The method of claim 12, wherein at least a portion of said gas-phase oxidant and at least a portion of said first slurry combine in said secondary reaction zone to form a second multi-phase reaction medium, wherein when the entire volume of said second multi-phase reaction medium is theoretically partitioned into 20 discrete horizontal slices of equal volume, no two adjacent horizontal slices have a combined time-averaged and volume-averaged oxygen content of less than 7 parts per million by weight ("ppmw").

18. The method of claim 17, wherein none of said horizontal slices has a time-averaged and volume-averaged oxygen content of less than 7 ppmw.

19. The method of claim 12, wherein said first and second slurries each comprise para-toluic acid in the liquid phase, wherein said second slurry has a time-averaged and volume-averaged concentration of liquid-phase para-toluic acid that is less than 50 percent of the time-averaged and volume-averaged concentration of liquid-phase para-toluic acid in said first slurry.

20. The method of claim 12, wherein said oxidizable compound is para-xylene, wherein said polycarboxylic acid is terephthalic acid, wherein said gas-phase oxidant is air.

21. The method of claim 12, wherein said primary oxidation reactor is a bubble column reactor, wherein said secondary oxidation reactor is a bubble column reactor.

22. The method of claim 12, wherein said reaction zone has an $L_S:D_S$ ratio in the range of from about 14:1 to about 28:1.

* * * * *